United States Patent
Sengun et al.

(10) Patent No.: US 9,345,468 B2
(45) Date of Patent: May 24, 2016

(54) SURGICAL FILAMENT SNARE ASSEMBLIES

(75) Inventors: Mehmet Ziya Sengun, Canton, MA (US); Howard Tang, Boston, MA (US); David B. Spenciner, Attleboro, MA (US); Gregory R. Whittaker, Stoneham, MA (US); Gerome Miller, Randolph, MA (US); Joseph Hernandez, Sandwich, MA (US); Robert Stefani, Shrewsbury, MA (US)

(73) Assignee: MEDOS INTERNATIONAL SÁRL, Le Locle (CH)

( * ) Notice: Subject to any disclaimer, the term of this patent is extended or adjusted under 35 U.S.C. 154(b) by 835 days.

(21) Appl. No.: 13/218,810

(22) Filed: Aug. 26, 2011

(65) Prior Publication Data

US 2012/0130424 A1 May 24, 2012

Related U.S. Application Data

(63) Continuation-in-part of application No. 12/977,154, filed on Dec. 23, 2010, now Pat. No. 8,814,905, and a continuation-in-part of application No. 12/977,146, filed on Dec. 23, 2010, now Pat. No. 8,821,543.

(60) Provisional application No. 61/416,562, filed on Nov. 23, 2010.

(51) Int. Cl.
*A61B 17/04* (2006.01)
*A61B 17/06* (2006.01)
*A61B 19/00* (2006.01)

(52) U.S. Cl.
CPC ....... *A61B 17/0401* (2013.01); *A61B 17/06166* (2013.01); *A61B 17/0482* (2013.01);

(Continued)

(58) Field of Classification Search
USPC ........... 606/60, 139, 145, 148, 228, 230, 232, 606/300; 289/1.2
See application file for complete search history.

(56) References Cited

U.S. PATENT DOCUMENTS

| 2,566,625 A | 9/1951 | Nagelmann |
| 2,600,395 A | 6/1952 | Domoj et al. |

(Continued)

FOREIGN PATENT DOCUMENTS

| AU | 2008229746 A1 | 10/2008 |
| CA | 2772500 A1 | 9/2013 |

(Continued)

OTHER PUBLICATIONS

[No Author Listed] Versalok Anchor. Brochure. DePuy Mitek, a Johnson & Johnson company, 92 pages, 2007.

(Continued)

*Primary Examiner* — Vy Bui

(57) ABSTRACT

A surgical filament snare assembly including an anchor capable of being fixated in bone and having a filament engagement feature. A first filament has a noose with first and second noose limbs connected, preferably slidably connected, to the filament engagement feature of the anchor. The first and second noose limbs emerge from the anchor as first and second free filament limbs which are capable of being passed through tissue to be repaired and then passable through the noose. The noose, such as one or more half-hitches, is capable of receiving the free filament limbs and strangulating them when tension is applied to at least one of the free filament limbs and the noose to enable incremental tensioning of the tissue after the anchor is fixated. Preferably, the snare assembly further includes a flexible sleeve joining at least some portion of the first and second free filament limbs to facilitate passing of the free filament limbs at least through the tissue as a single unit.

14 Claims, 26 Drawing Sheets

(52) U.S. Cl.
CPC ....... *A61B17/0485* (2013.01); *A61B 2017/044* (2013.01); *A61B 2017/0448* (2013.01); *A61B 2017/0456* (2013.01); *A61B 2017/0458* (2013.01); *A61B 2017/0464* (2013.01); *A61B 2017/0475* (2013.01); *A61B 2017/06185* (2013.01); *A61B 2019/4836* (2013.01)

(56) References Cited

U.S. PATENT DOCUMENTS

| | | |
|---|---|---|
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A * | 4/1995 | Weston ........................ 606/148 |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 * | 7/2004 | Wenstrom, Jr. ................ 289/1.2 |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |

(56) References Cited

U.S. PATENT DOCUMENTS

| | | | |
|---|---|---|---|
| 7,883,529 B2 | 2/2011 | Sinnott et al. | |
| 7,905,903 B2 | 3/2011 | Stone et al. | |
| 7,905,904 B2 | 3/2011 | Stone et al. | |
| 7,959,650 B2 * | 6/2011 | Kaiser et al. | 606/232 |
| 7,981,140 B2 | 7/2011 | Burkhart | |
| 8,012,171 B2 | 9/2011 | Schmieding | |
| 8,088,146 B2 | 1/2012 | Wert et al. | |
| 8,114,128 B2 | 2/2012 | Cauldwell et al. | |
| 8,118,836 B2 | 2/2012 | Denham et al. | |
| 8,137,382 B2 | 3/2012 | Denham et al. | |
| 8,231,653 B2 | 7/2012 | Dreyfuss | |
| 8,231,654 B2 | 7/2012 | Kaiser et al. | |
| 8,419,769 B2 | 4/2013 | Thal | |
| 8,545,535 B2 | 10/2013 | Hirotsuka et al. | |
| 8,790,370 B2 | 7/2014 | Spenciner et al. | |
| 8,814,905 B2 * | 8/2014 | Sengun et al. | 606/232 |
| 8,821,543 B2 | 9/2014 | Hernandez et al. | |
| 8,821,544 B2 | 9/2014 | Sengun et al. | |
| 8,821,545 B2 | 9/2014 | Sengun | |
| 8,894,684 B2 | 11/2014 | Sengun | |
| 8,974,495 B2 | 3/2015 | Hernandez et al. | |
| 9,017,381 B2 | 4/2015 | Kaiser et al. | |
| 9,034,013 B2 | 5/2015 | Sengun | |
| 9,060,763 B2 | 6/2015 | Sengun | |
| 9,060,764 B2 | 6/2015 | Sengun | |
| 9,095,331 B2 | 8/2015 | Hernandez et al. | |
| 2002/0019649 A1 | 2/2002 | Sikora et al. | |
| 2002/0029066 A1 | 3/2002 | Foerster | |
| 2003/0004545 A1 | 1/2003 | Burkhart et al. | |
| 2003/0050667 A1 | 3/2003 | Grafton et al. | |
| 2003/0120309 A1 | 6/2003 | Colleran et al. | |
| 2003/0130695 A1 | 7/2003 | McDevitt et al. | |
| 2003/0229362 A1 | 12/2003 | Chan et al. | |
| 2004/0093031 A1 | 5/2004 | Burkhart et al. | |
| 2004/0098050 A1 | 5/2004 | Foerster et al. | |
| 2004/0153074 A1 | 8/2004 | Bojarski et al. | |
| 2004/0172062 A1 | 9/2004 | Burkhart | |
| 2004/0236373 A1 | 11/2004 | Anspach | |
| 2005/0033363 A1 | 2/2005 | Bojarski et al. | |
| 2005/0119696 A1 | 6/2005 | Walters et al. | |
| 2005/0137624 A1 | 6/2005 | Fallman | |
| 2005/0187577 A1 | 8/2005 | Selvitelli et al. | |
| 2005/0251208 A1 | 11/2005 | Elmer et al. | |
| 2006/0106423 A1 | 5/2006 | Weisel et al. | |
| 2006/0178680 A1 | 8/2006 | Nelson et al. | |
| 2006/0178702 A1 | 8/2006 | Pierce et al. | |
| 2006/0293710 A1 | 12/2006 | Foerster et al. | |
| 2007/0027476 A1 | 2/2007 | Harris et al. | |
| 2007/0032792 A1 | 2/2007 | Collin et al. | |
| 2007/0060922 A1 | 3/2007 | Dreyfuss | |
| 2007/0083236 A1 | 4/2007 | Sikora et al. | |
| 2007/0135843 A1 | 6/2007 | Burkhart | |
| 2007/0150003 A1 | 6/2007 | Dreyfuss et al. | |
| 2007/0156148 A1 | 7/2007 | Fanton et al. | |
| 2007/0156149 A1 | 7/2007 | Fanton et al. | |
| 2007/0156150 A1 | 7/2007 | Fanton et al. | |
| 2007/0156176 A1 | 7/2007 | Fanton et al. | |
| 2007/0219557 A1 | 9/2007 | Bourque et al. | |
| 2007/0219558 A1 | 9/2007 | Deutsch | |
| 2007/0225719 A1 | 9/2007 | Stone et al. | |
| 2007/0239209 A1 | 10/2007 | Fallman | |
| 2008/0009901 A1 | 1/2008 | Redmond et al. | |
| 2008/0009904 A1 | 1/2008 | Bourque et al. | |
| 2008/0027446 A1 | 1/2008 | Stone et al. | |
| 2008/0065114 A1 | 3/2008 | Stone et al. | |
| 2008/0077182 A1 | 3/2008 | Geissler et al. | |
| 2008/0091237 A1 | 4/2008 | Schwartz et al. | |
| 2008/0103528 A1 | 5/2008 | Zirps et al. | |
| 2008/0140092 A1 | 6/2008 | Stone et al. | |
| 2008/0147063 A1 | 6/2008 | Cauldwell et al. | |
| 2008/0188893 A1 | 8/2008 | Selvitelli et al. | |
| 2008/0195205 A1 | 8/2008 | Schwartz | |
| 2008/0208265 A1 | 8/2008 | Frazier et al. | |
| 2008/0228265 A1 | 9/2008 | Spence et al. | |
| 2008/0255613 A1 | 10/2008 | Kaiser et al. | |
| 2008/0275469 A1 | 11/2008 | Fanton et al. | |
| 2008/0312689 A1 | 12/2008 | Denham et al. | |
| 2009/0023984 A1 | 1/2009 | Stokes et al. | |
| 2009/0036905 A1 | 2/2009 | Schmieding | |
| 2009/0054928 A1 | 2/2009 | Denham et al. | |
| 2009/0062850 A1 | 3/2009 | Ken | |
| 2009/0062854 A1 | 3/2009 | Kaiser et al. | |
| 2009/0082805 A1 | 3/2009 | Kaiser et al. | |
| 2009/0082807 A1 | 3/2009 | Miller et al. | |
| 2009/0088798 A1 | 4/2009 | Snyder et al. | |
| 2009/0099598 A1 | 4/2009 | McDevitt et al. | |
| 2009/0138042 A1 | 5/2009 | Thal | |
| 2009/0281568 A1 | 11/2009 | Cendan et al. | |
| 2009/0281581 A1 | 11/2009 | Berg | |
| 2009/0287246 A1 | 11/2009 | Cauldwell et al. | |
| 2009/0306711 A1 | 12/2009 | Stone et al. | |
| 2009/0312776 A1 | 12/2009 | Kaiser et al. | |
| 2009/0312794 A1 | 12/2009 | Nason et al. | |
| 2009/0318958 A1 | 12/2009 | Ochiai | |
| 2010/0004683 A1 | 1/2010 | Hoof et al. | |
| 2010/0016892 A1 | 1/2010 | Kaiser et al. | |
| 2010/0094425 A1 | 4/2010 | Bentley et al. | |
| 2010/0162882 A1 | 7/2010 | Shakespeare | |
| 2010/0204730 A1 | 8/2010 | Maiorino et al. | |
| 2010/0249809 A1 | 9/2010 | Singhatat et al. | |
| 2010/0249834 A1 | 9/2010 | Dreyfuss | |
| 2010/0256677 A1 | 10/2010 | Albertorio et al. | |
| 2010/0292732 A1 | 11/2010 | Hirotsuka et al. | |
| 2010/0292792 A1 | 11/2010 | Stone et al. | |
| 2011/0022083 A1 | 1/2011 | DiMatteo et al. | |
| 2011/0022084 A1 | 1/2011 | Sengun et al. | |
| 2011/0077667 A1 | 3/2011 | Singhatat et al. | |
| 2011/0190815 A1 | 8/2011 | Saliman | |
| 2011/0208240 A1 | 8/2011 | Stone et al. | |
| 2011/0213416 A1 | 9/2011 | Kaiser | |
| 2011/0238111 A1 | 9/2011 | Frank | |
| 2011/0264141 A1 | 10/2011 | Denham et al. | |
| 2011/0270278 A1 | 11/2011 | Overes et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0101523 A1 | 4/2012 | Wert et al. | |
| 2012/0130423 A1 | 5/2012 | Sengun et al. | |
| 2012/0150223 A1 | 6/2012 | Manos et al. | |
| 2012/0165864 A1 | 6/2012 | Hernandez et al. | |
| 2012/0179199 A1 | 7/2012 | Hernandez et al. | |
| 2012/0253389 A1 | 10/2012 | Sengun et al. | |
| 2012/0253390 A1 | 10/2012 | Sengun | |
| 2012/0296375 A1 | 11/2012 | Thal | |
| 2013/0110165 A1 | 5/2013 | Burkhart et al. | |
| 2013/0158598 A1 | 6/2013 | Lizardi | |
| 2013/0261664 A1 | 10/2013 | Spenciner et al. | |
| 2013/0296895 A1 | 11/2013 | Sengun | |
| 2013/0296896 A1 | 11/2013 | Sengun | |
| 2013/0296931 A1 | 11/2013 | Sengun | |
| 2013/0296934 A1 | 11/2013 | Sengun | |
| 2014/0081324 A1 | 3/2014 | Sengun | |
| 2014/0188163 A1 | 7/2014 | Sengun | |
| 2014/0188164 A1 | 7/2014 | Sengun | |
| 2014/0277132 A1 | 9/2014 | Sengun et al. | |
| 2014/0330312 A1 | 11/2014 | Spenciner et al. | |
| 2014/0343606 A1 | 11/2014 | Hernandez et al. | |
| 2014/0343607 A1 | 11/2014 | Sengun et al. | |
| 2015/0012038 A1 | 1/2015 | Sengun et al. | |
| 2015/0025572 A1 | 1/2015 | Sengun | |
| 2015/0045832 A1 | 2/2015 | Sengun | |
| 2015/0238183 A1 | 8/2015 | Sengun | |
| 2015/0245832 A1 | 9/2015 | Sengun | |

FOREIGN PATENT DOCUMENTS

| | | |
|---|---|---|
| EP | 0870471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| JP | 2000-512193 A | 9/2000 |
| WO | 9519139 A1 | 7/1995 |

(56) References Cited

FOREIGN PATENT DOCUMENTS

| WO | 9717901 A1 | 5/1997 |
|---|---|---|
| WO | 9811825 A1 | 3/1998 |
| WO | 98/42261 A1 | 10/1998 |
| WO | 01/06933 A2 | 2/2001 |
| WO | 03/022161 A1 | 3/2003 |
| WO | 2007/109769 A1 | 9/2007 |

OTHER PUBLICATIONS

EP Search Report for Application No. 11190159.1 issued Feb. 21, 2012. (8 pages).

EP Search Report for Application No. 11190157.5 issued Feb. 27, 2012. (8 pages).

Dahl et al., Biomechanical characteristics of 9 arthroscopic knots. Arthroscopy. Jun. 2010;26(6):813-8.

[No Author Listed] Arthroscopic Knot Tying Manual 2005. DePuy Mitek.

Kemnitzer et al., Handbook of biodegradable Polymers. Eds. Domb et al. Hardwood Acad. Press. 1997;251-72.

Cohn et al., Biodegradable PEO/PLA block copolymers. J Biomed Mater Res. Nov. 1988;22(11):993-1009.

Cohn et al., Polym Preprint. 1989;30(1):498.

Allock, The Encyclopedia of Polymer Science, vol. 13, pp. 31-41, Wiley Intersciences, John Wiley & Sons, 1988.

Vandorpe et al., Handbook of Biodegradable Polymers, edited by Domb, et al., Hardwood Acad. Press, pp. 161-182 (1997).

Heller, Handbook of Biodegradable Polymers, edited by Domb, et al., Hardwood Academic Press, pp. 99-118 (1997).

Extended European Search Report for Application No. 11190159.1 issued Jul. 6, 2012. (11 pages).

Extended European Search Report for Application No. 11190157.5 issued Jul. 6, 2012. (10 pages).

Extended European Search Report for Application No. 13199724.9 issued Apr. 4, 2014 (6 Pages).

International Search Report for Application No. PCT/US2011/067119, mailed Jun. 4, 2012. (6 pages).

Extended European Search Report for Application No. 13166905.3 issued Aug. 13, 2013 (9 Pages).

Extended European Search Report for Application No. 13166907.9, issued Aug. 1, 2013 (6 pages).

Extended European Search Report for Application No. 13166908.7, issued Aug. 23, 2013 (8 pages).

Extented European Search Report for Application No. 11195100.0 issued Oct. 17, 2012. (7 pages).

Extended European Search Report for Application No. 13185425.9 issued Dec. 16, 2013 (9 Pages).

[No Author Listed] Gryphon Brochure. DePuy Mitek. 2 pages (undated).

Japanese Office Action for Application No. 2011-281088, issued Nov. 10, 2015 (4 pages).

* cited by examiner

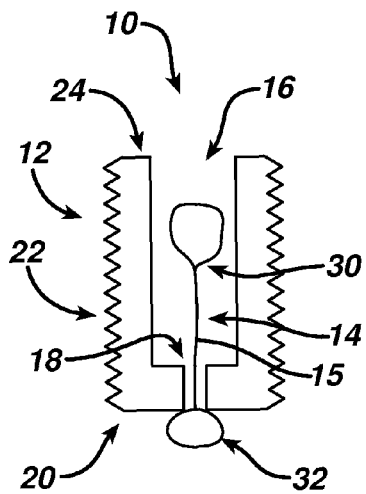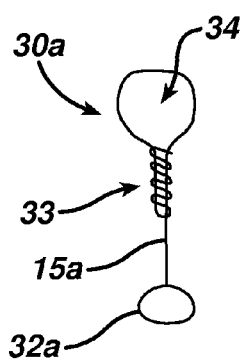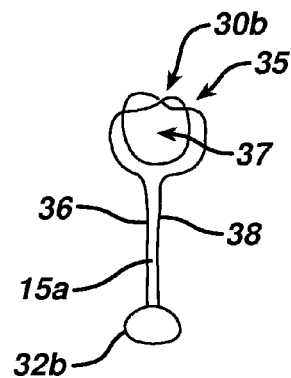
FIG. 1  FIG. 1A  FIG. 1B
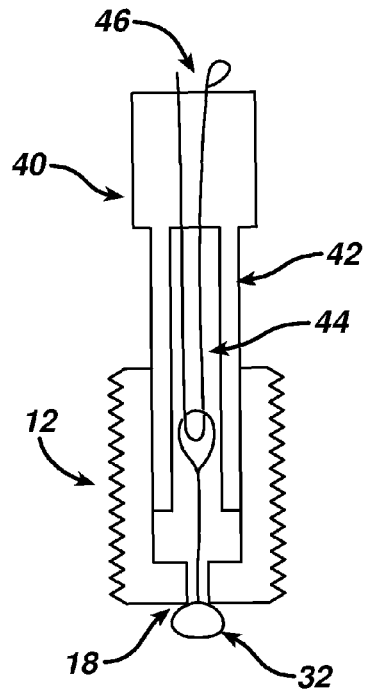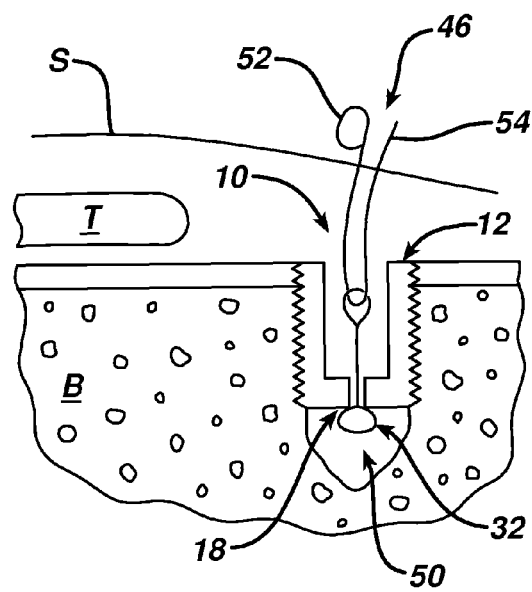
FIG. 2  FIG. 3

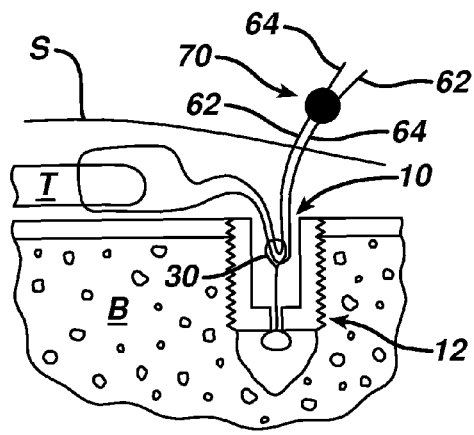
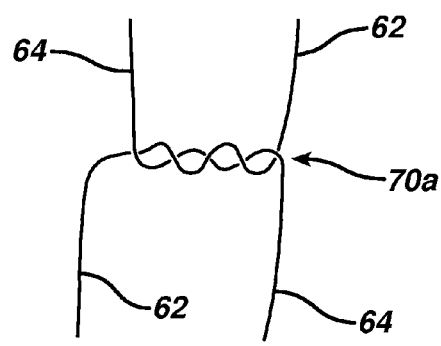
FIG. 8  FIG. 8A
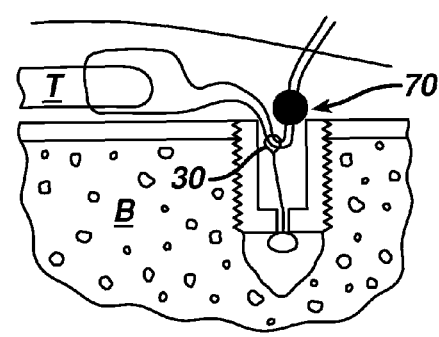
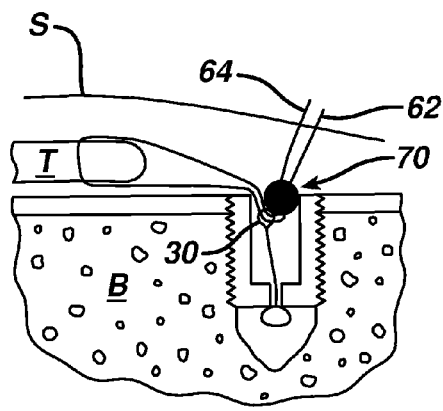
FIG. 9  FIG. 10

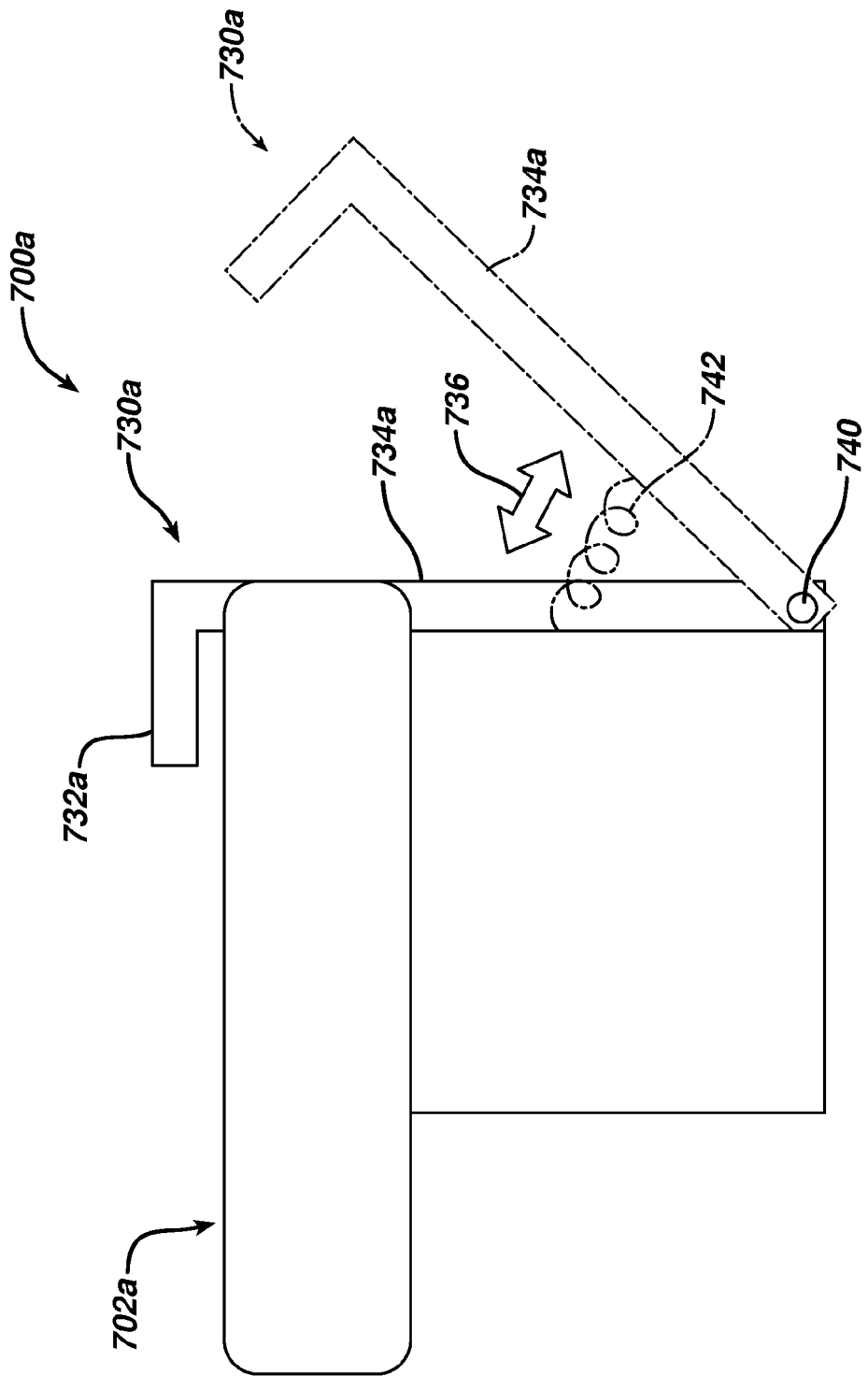

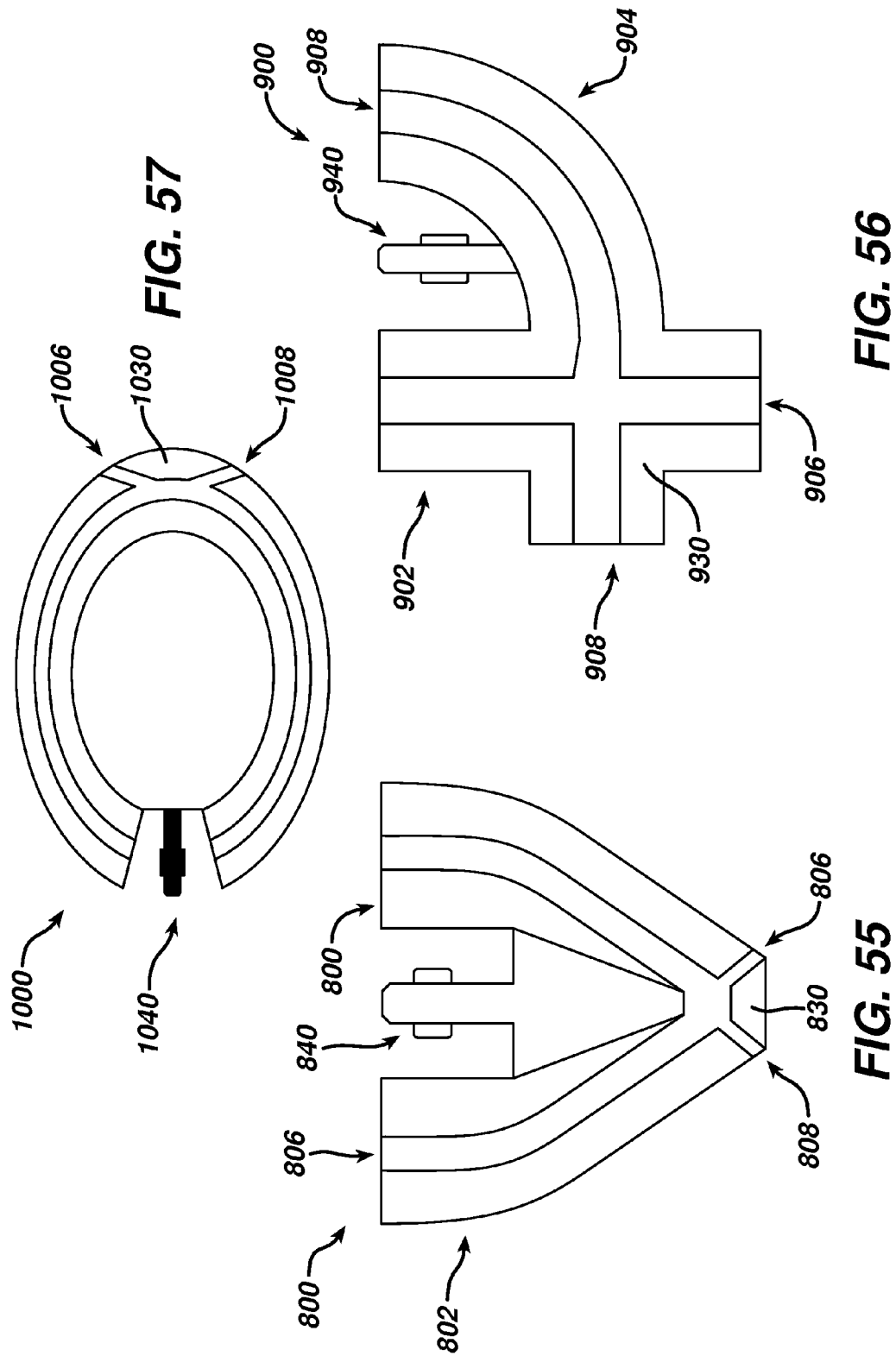

SURGICAL FILAMENT SNARE ASSEMBLIES

CROSS-REFERENCE TO RELATED APPLICATIONS

This application claims priority to U.S. Provisional Application No. 61/416,562 filed 23 Nov. 2010 which is a provisional of U.S. patent application Ser. No. 12/977,154 filed Dec. 23, 2010, this application also claims priority to U.S. patent application Ser. No. 12/977,146 which was filed Dec. 23, 2010.

BACKGROUND OF THE INVENTION

1. Field of the Invention

The invention relates to filament assemblies for securing tissue to bone and more particularly to adjustable tensioning of tissue independent of anchor fixation.

2. Description of the Related Art

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors and tacks.

Arthroscopic knot tying is commonly practiced in shoulder rotator cuff and instability procedures. Typically, an anchor loaded with suture is attached to bone first. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

Surgeons typically tie the suture ends by first placing a surgical sliding knot such as the Tennessee Slider or Duncan Knot. After tightening the loop, a number of additional half hitches or other knots are tied. The additional knots are needed because a conventional sliding knot does not provide the necessary protection against loosening or slippage, especially when tension is placed primarily on the limbs of the loop. Generally accepted practice is to follow the sliding knot with at least three reversed half hitches on alternating posts of the suture.

Before one or more half hitches or other knots can be added to the sliding knot, however, there exists a potential for the sliding knot to slip, that is, for the loop to enlarge as the tissue places tension on the loop. This has been referred to as "loop security" and can reportedly occur even in the hands of very experienced surgeons. Sometimes, even fully-tied knots may slip. Further, the overall size of a conventional knot can be obstructive or intrusive, especially in tight joints, which may damage cartilage or other tissue by abrasion with the knot.

Suture anchor systems with sliding and locking knots for repairing torn or damaged tissue include U.S. Pat. No. 6,767,037 by Wenstrom, Jr. Other suture anchor systems suited especially for meniscal repair are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767.

There are a number of suture implant systems which proclaim to be "knotless", that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors which capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042. Other systems having clamps or other locking mechanisms include U.S. Pat. No. 5,702,397 by Goble et al. and U.S. Patent Application Publication No. 2008/0091237 by Schwartz et al.

It is therefore desirable to have robust yet adjustable fixation of tissue while minimizing both the number and size of knots to be tied by a surgeon, especially during arthroscopic repair procedures.

SUMMARY OF THE INVENTION

An object of the present invention is to meet or exceed the tissue tension control and holding power of currently available suture anchor assemblies for tissue repair procedures while reducing the number of half hitches or other knots to be tied by a surgeon.

Another object of the present invention is to reduce the size of the finished knot for the assembly.

A still further object is to simplify the overall knot tying process for the surgeon while providing enhanced loop security and knot security Yet another object of the present invention is to provide incremental tensioning after anchor fixation.

This invention features a surgical filament snare assembly including an anchor capable of being fixated in bone and having a filament engagement feature. A first filament has a noose with first and second noose limbs connected, preferably slidably connected, to the filament engagement feature of the anchor. The first and second noose limbs emerge from the anchor as first and second free filament limbs which are capable of being passed through tissue to be repaired and then passable through the noose. The noose, such as one or more half-hitches, is capable of receiving the free filament limbs and strangulating them when tension is applied to at least one of the free filament limbs and the noose to enable incremental tensioning of the tissue after the anchor is fixated. Preferably, the snare assembly further includes a flexible sleeve joining at least some portion of the first and second free filament limbs to facilitate passing of the free filament limbs at least through the tissue as a single unit.

In preferred embodiments, the sleeve is formed from a braided suture. In certain embodiments, the first filament is a braided suture and a section of one of the first and second free filament limbs serves as the sleeve. In one embodiment, the sleeve section has fewer picks, preferably at least ten percent fewer, per unit length than the picks per unit length for the remainder of the first filament. In certain embodiments, the sleeve is positioned over the entire portion of the first and second filaments before implantation of the anchor in the patient, and in some embodiments the sleeve is further positioned beyond the filament engagement feature to cover at least some of the first and second noose limbs.

In some embodiments, the noose is retractable toward the anchor. A tool with at least one projection such as a tube may be included to assist passing the free filament limb through the noose. In certain embodiments wherein the noose is formed from at least one half hitch, the assembly includes at least two tubes capable of being removably inserted into different loops of the half hitch to provide passages for two ends of free filament limbs. In some embodiments, the tubes are joined together and have at least one handle for manipulating the tubes. Preferably, each tube is slotted to facilitate removal of the free filament limbs from the tubes.

This invention may be expressed as a method of surgically repairing tissue, preferably utilizing a sleeve, by selecting an anchor capable of being fixated in bone and having a filament engagement feature. A first filament is selected having a noose with first and second noose limbs connected, preferably slidably connected, to the filament engagement feature of the anchor. The first and second noose limbs emerge from the anchor as first and second free filament limbs which are capable of being passed through tissue to be repaired and then passable through the noose. Preferably a flexible sleeve, joining at least some portion of the first and second free filament limbs, is also selected to facilitate passing of the free filament limbs at least through the tissue as a single unit. The anchor is fixated in bone, and at least the sleeve is passed through the tissue to be repaired. At least the free filament limbs, preferably with the sleeve, are passed through the noose. The tissue is then tensioned as desired with the noose strangulating the free filament limbs when tension is applied to at least one of the free filament limbs and the noose to enable incremental tensioning of the tissue after the anchor is fixated. The sleeve is removed from the patient.

This invention also features a surgical filament snare assembly having an anchor capable of being fixated in bone and having a filament engagement feature, and a first filament having a fixed-length loop, capable of being passed through tissue and capable of being formed into a noose, on a first portion of at least a first limb and having a second portion. The assembly further includes a second filament having a collapsible loop slidably attached to the second portion of the first filament, the collapsible loop being formed by a sliding knot with a tensioning limb. The tensioning limb and the sliding knot are capable of being passed through the noose to enable incremental tensioning of the tissue after the anchor is fixated in bone, with the noose strangulating the collapsible loop when tension is applied to at least one of the free suture limb and the noose. At least one of the first filament and the second filament are slidably connected to the filament engagement feature of the anchor.

In some embodiments, the first filament is formed as a continuous loop, and the collapsible loop is slidably connected to the filament engagement feature.

This invention may also be expressed as a method of surgically repairing tissue with a fixed-length loop by selecting an anchor capable of being fixated in bone and having a filament engagement feature. A first filament is selected having a fixed-length loop, capable of being passed through tissue to be repaired and capable of being formed into a noose, on a first portion of at least a first limb and having a second portion slidably attached to a collapsible loop of a second filament, the collapsible loop being formed by a sliding knot with a tensioning limb, the tensioning limb and the sliding knot capable of being passed through the noose. The anchor is fixated in bone, and at least a portion of the fixed-length loop is passed through the tissue to be repaired. A portion of the fixed-length loop is formed into a Lark's Head knot to serve as the noose. The tissue is then tensioned as desired with the noose strangulating the collapsible loop when tension is applied to at least one of the tensioning limb, the sliding knot and the noose to enable incremental tensioning of the tissue after the anchor is fixated.

This invention further features a surgical filament snare assembly with a bone anchor and a first filament having a noose, formed from at least one half hitch, on a first portion of at least a first limb and having a second portion connected to the filament engagement feature of the anchor. The noose is capable of receiving at least two free filament limbs and strangulating them when tension is applied to at least one of the free filament limbs and the noose. Preferably, the assembly further includes a threader tool having at least two projections having distal ends capable of being removably inserted into different loops of the half hitch. Each projection defines a channel capable of receiving a portion of at least one free filament limb to pass it through a loop of the half hitch, and each projection further defines a slot communicating with the channel to facilitate removal of the filament limb from the tool.

In certain embodiments, the projections are tubes joined together with at least one handle for manipulation the tube. The proximal ends of the channels are connected by one of an intersection and a common passage, and the tool further includes a stop as a proximal portion of the one of the intersection and the common passage. In some embodiments, the stop is movable, and may include a spring to bias the stop toward the intersection or common passage. In yet other embodiments, the assembly further includes at least two suture passers having distal ends for engaging portions of the free filament limbs, and the suture passers capable of pulling the free filament limbs through the channels when proximal-directed force is applied to proximal ends of the suture passers.

This invention may yet also be expressed as a method of creating a surgical filament snare assembly by selecting a first filament having first and second ends, and forming at least one half hitch with a central opening in the first filament between the first and second ends. The first and second ends are passed through the central opening to define a noose with first and second noose limbs, and the half hitch is tightened to form a slidable knot for the noose. The first and second filament ends are passed through a filament engagement feature of an anchor to emerge from the anchor as first and second free filament limbs which are capable of being passed through tissue to be repaired and then passable through the noose, the noose strangulating the free filament limbs when tension is applied to at least one of the free filament limbs and the noose opening.

BRIEF DESCRIPTION OF THE DRAWINGS

In what follows, preferred embodiments of the invention are explained in more detail with reference to the drawings, in which:

FIG. 1 is a schematic side view of a surgical filament snare assembly according to the present invention having an anchor and a noose;

FIG. 1A is a schematic side view of a hangman-type noose and FIG. 1B is such a view of a half-hitch noose to be utilized according to the present invention;

FIG. 2 is a schematic side view of the assembly of FIG. 1 removably connected with a cannulated driver for initially fixating the anchor with a threader loop passed through the noose;

FIGS. 3-10 are schematic side views illustrating a process for capturing and tensioning tissue to the surgical filament snare assembly according to the present invention, with FIG. 8A providing an example of a stopper knot shown in FIGS. 8, 9 and 10;

FIG. 54 is a schematic side view of an alternative threader tool with a movable stop; and FIGS. 55-57 are schematic top views of yet other threader tools according to the present invention with different fixed-stop configurations.

DETAILED DESCRIPTION OF THE PRESENTLY PREFERRED EMBODIMENTS

Figure 4:
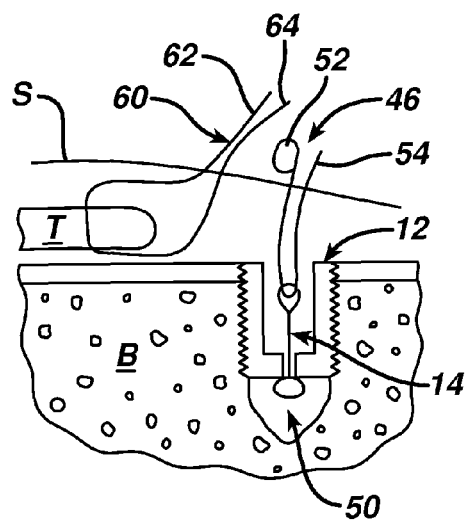

This invention may be accomplished by a surgical filament snare assembly including an anchor capable of being fixated in bone and having a filament engagement feature. A first filament has a noose, or a loop capable of being formed into a noose, on a first, proximal portion of at least a first limb and has a second portion connected, including slidably or fixedly connected, directly or indirectly, to the filament engagement feature of the anchor. The noose, such as one or more half-hitches, a Lark's Head knot, or a hangman-type noose, is capable of receiving at least one end of a free filament limb or a portion of another filament. The noose strangulates the free filament limb or other filament when tension is applied to the noose, to the free filament limb, and/or to the other filament.

In certain preferred constructions, at least a first free filament limb, which in some constructions is a length of the first filament and in other constructions is a second filament, is passed through tissue to be repaired and has at least one end passable through the noose to enable incremental tensioning of the tissue after the anchor is fixated in bone. The present application is directed to one or more improvements described below beginning with FIG. 29.

Surgical filament snare assembly 10, FIG. 1, has an anchor 12 and a first filament 14. In this construction, anchor 12 defines an internal passage 16 with a restricted opening 18 at its distal end 20 which serves as a filament engagement feature. At least one bone-engaging feature 22, such as an external rib or helical thread, is located on the outer surface of anchor 12 between distal end 20 and proximal end 24.

First filament 14 has a noose 30 at its proximal end and a fixed knot 32 at the distal end of filament post or stem 15 which interacts with restricted opening 18 to retain filament 14 in a fixed, permanently attached position. This arrangement may be referred to as the first filament 14 connected with the filament engagement feature 18, which includes the phrase passing through the filament engagement feature 18. Many conventional knots, such as a mulberry knot, can be utilized for fixed knot 32 as long as knot 32 has sufficient bulk to prevent pull-through at clinically desired tensions on noose 30. A number of other types of filament engagements are described below. Stem 15 is kept as short as possible to maintain noose 30 close to anchor 12 even after it is collapsed as described below.

A well-known noose knot 33 is illustrated in FIG. 1A in which first filament 14a has a hangman-type noose 30a at its proximal end and a fixed knot 32a at the distal end of stem 15a. Noose 30a has sliding noose knot 33 and defines an opening 34. Noose knot 33 is tied by forming a flattened "S" or "Z" shape at the proximal end of filament 14a to form a large proximal loop to serve as the noose opening and a small loop spaced from the large loop. The doubled filament limbs are wrapped with the terminal end, also known as the working end. After typically four to eight wrapping turns, the terminal end is tucked through the small loop and trapped by pulling on whichever of the limbs of the large loop closes the small loop.

An alternative, simpler noose is illustrated for first filament 14b, FIG. 1B, having a half hitch 35, also referred to as a simple or overhand knot, tied to form noose 30b in the middle of filament limbs 36 and 38. Multiple openings are created by the loops in half hitch 35 as described in more detail below, although central opening 37 is shown as a large single opening in FIG. 1B. First filament limbs 36 and 38 are folded around half hitch 35 to form a double-stem arrangement, and the distal ends of first filament limbs 36 and 38 are joined in knot 32b after being passed through a suitable filament engagement feature on an anchor.

Noose efficiency is defined herein as the strangulation strength per unit tension applied on the noose, either by pulling on the filament on which the noose is tied or which otherwise carries the noose, or by pulling on one or more strands or limbs of filaments passing through the noose. A noose with lower internal friction in the noose knot will tend to have a higher noose efficiency.

One instrument for inserting anchor 12 into a hole drilled in bone is illustrated in FIG. 2. Driver 40 has a distal end 42 removably insertable into passage 16. Driver 40 is cannulated in this construction and has a lumen 44 with an optional threader filament 46 that passes through noose 30. Use of a threader filament is optional, but may be desirable when noose 30 is spaced only a short distance from filament engagement feature 18, in other words, when noose 30 is initially positioned close to or inside of anchor 12.

In one procedure according to the present invention, anchor 12 is shown fixated within bone B, FIG. 3, after driver 40 has been removed, in a hole 50 spaced at a desired distance from tissue T to be repaired. Noose 30 is in an initial open configuration. Threader filament 46 has a sufficient length to have both a threader loop 52 on a first limb, and a graspable portion on a second limb 54, extend proximally above skin S while a mid-portion of threader filament 46 is slidably associated with noose 30.

Figure 5:
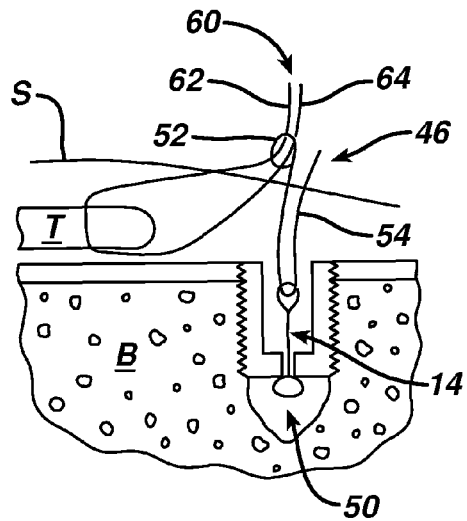
Figure 6:
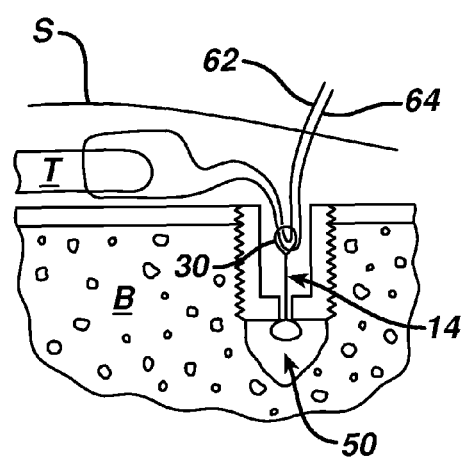

Continuing with this exemplary procedure, a second filament 60, FIG. 4, is threaded through tissue T using a suture passing instrument, a needle, or other tissue-penetrating technique chosen by a surgeon. Both free filament limbs 62 and 64 are brought together, typically above skin S, or at least outside of a joint space, and passed through threader loop 52, FIG. 5. Threader limb 54 is then pulled to thread both second filament limbs 62 and 64 through noose 30 as illustrated in FIG. 6 while noose 30 is in the initial open configuration. Alternatively, free filament limbs 62 and 64 are passed directly through noose 30 without using a threader filament.

Figure 7:
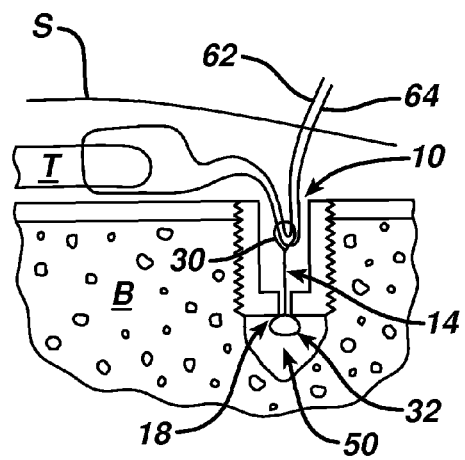
Figure 13:
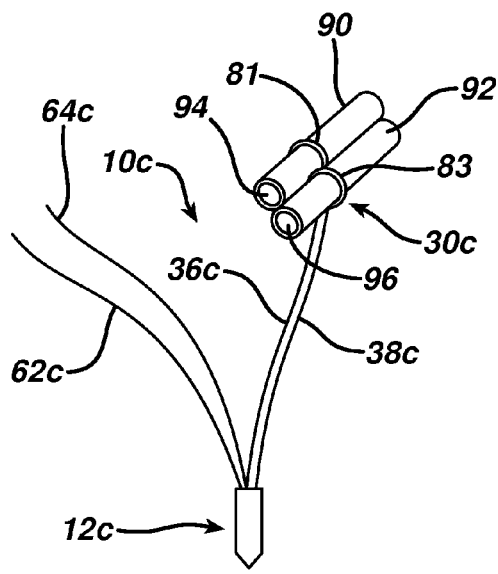
FIG. 13 is a perspective view of tubes to assist threading of free filament limbs through noose openings of FIG. 11.
Figure 14B:
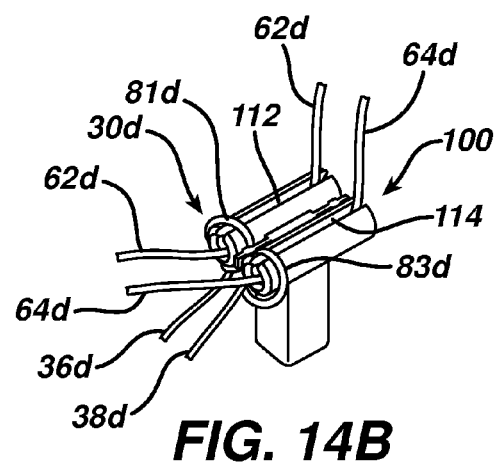
FIG. 14B shows the device of FIG. 14A being utilized to thread a noose.

When there is high noose efficiency, a light tug is sufficient to collapse noose 30 on the filament limbs 62 and 64 as shown in FIG. 7 to provide initial tensioning on the surgical filament snare assembly 10. Generally, a higher noose efficiency can be utilized when one or more free filament limbs are threaded directly through noose 30 without using a threader filament, or are threaded using a tube or threader device such as shown in FIGS. 13-14B below.

After initial or pre-tensioning of free filament limbs 62 and 64, FIG. 7, tension is released on limbs 62, 64 and a slidable stopper knot 70, FIG. 8, is tied by the surgeon on limbs 62, 64 above skin S. An enlarged view of one construction for stopper knot 70a, FIG. 8A, shows a half hitch with an extra throw or turn, also known as a double overhand knot. A simple knot such as a single half hitch or overhand knot may be sufficient for some situations. Other suitable, more robust surgeon slidable knots with higher load capacity include the Tennessee Slider described in the Arthroscopic Knot Tying Manual (2005) available from DePuy Mitek, as well as the slidable, lockable knot by Wenstrom, Jr. in U.S. Pat. No. 6,767,037. Alternatively, a mechanical locking mechanism may be utilized where overall profile is not critical, especially away from a joint or other articulating surfaces.

Stopper knot 70 is advanced, typically using a knot pusher, until it contacts noose 30, FIG. 9. Tension generated between tissue T and anchor 12, alone or together with pulling on one of the filament limbs 62 or 64, causes noose 30 to further collapse, FIG. 10, and strangulate the filaments. Stopper knot 70 augments the strangulation by transferring all tissue-generated tension on the stopper knot to the noose 30 and preventing slippage of filament limbs 62, 64 into the noose knot. Accordingly, a self-cinching mechanism is created which inhibits loosening of the filaments. Tension can be increased incrementally in a ratchet-like effect by further advancing the stopper knot or pulling on one of filament limbs 62, 64.

Once satisfactory tissue tension has been achieved, one or more half hitches may be added to stopper knot 70 to fortify the loading capacity on the stopper knot and reduce the risk of loosening under adverse conditions. By comparison, conventional sliding knots typically are reinforced by at least two or three reversed half hitches placed on alternating posts. Due to the self-cinching effect of the present invention, fewer overall hitches or other knots are needed for stopper knot 70 to meet or exceed the load performance relative to conventional knot systems. The present invention thereby accomplishes a lower overall knot profile to handle a given load. Limbs 62, 64 are trimmed as desired. The stopper knot also minimizes fraying of the filament ends over time.

Preferred materials for filaments 14 and 60 include various surgical sutures, typically size 0 to size 5, such as Orthocord™ suture commercially available from DePuy Mitek, and Ethibond™ suture available from Ethicon. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. The amount and type of bioabsorbable material, if any, utilized in the first or second filament is primarily a matter of surgeon preference for the particular surgical procedure to be performed.

While the same type of suture, even identical suture, can be used for both first, noose filament 14 and second, tissue filament 60, a suture having a lower abrasive property at its surface may be preferred by some surgeons for second filament 60. The lower abrasive property can be achieved by a larger diameter, a softer composition, a softer braid, plait or strand pattern, or a combination of such characteristics. The term "braid" as utilized herein includes "plait" and other multifilament patterns.

Figure 11:
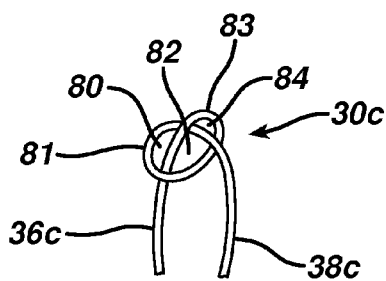
FIGS. 11 and 12 are perspective views of an alternative half-hitch noose in which multiple openings are utilized to strangulate two or more free filament limbs.
Figure 12:
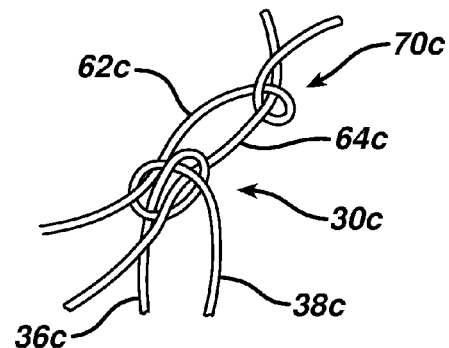

The nooses illustrated in FIGS. 1-6 above have been described as having a single opening through which one or more free filament limbs are threaded. A simple half hitch or overhand-type "pretzel"-like knot is illustrated in FIG. 11 for noose 30c having multiple useful openings 80, 82 and 84. Side openings 80 and 84 are formed by minor loops 81 and 83 of the half hitch knot in first filament limbs 36c, 38c while central opening 82 is formed by the major loop. Free filament limbs 62c and 64c are shown in FIG. 12 extending through side opening 80 and central opening 82, respectively, although other combinations and permutations, such as using side openings 80 and 84, or central opening 82 and side opening 84, are also effective. Utilizing different areas or regions of the noose knot significantly increases effective strangulation and gripping on the free filament limbs. It is expected that utilizing multiple openings in the noose knot also minimizes any dependence of load carrying capacity on filament compliance characteristics. A simple, single half hitch stopper knot 70c is also illustrated in FIG. 12.

While two or more threader filaments, or careful, potentially tedious manipulation by a surgeon, could be utilized to achieve the configuration shown in FIG. 12, an alternative technique which avoids inadvertent noose collapse is shown in FIG. 13. Tubes 90 and 92 have outer diameters suitable for sliding into the side openings formed by loops 81 and 83. Filament limbs 36, 38c are shown engaged with anchor 12c. Tubes 90 and 92 define passages 94 and 96, respectively, through which free filament limbs 62c and 64c are threaded. Tubes 90 and 92 are then disengaged from noose 30c and drawn proximally along filament limbs 62c and 64c until they can be removed and discarded appropriately.

Figure 14A:
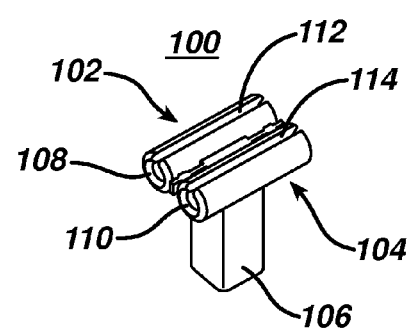
FIG. 14A is a perspective view of a double-barreled, slotted threader device.

Double-barrelled threader device 100, FIG. 14A, has two threader tubes 102, 104 which are joined together with a handle 106 and provide an even easier technique. In one construction, device 100 is molded as a monolithic unit using a polymer material. Tubes 102, 104 have internal lumens 108, 110, respectively, also referred to herein as channels, with openings at both ends as well as slots 112, 114, respectively, which also run the entire length of tubes 102, 104. During use, tubes 102, 104 are placed through loops 81d, 83d, FIG. 14B, formed from first filament limbs 36d, 38d, and free filament limbs 62d, 64d are inserted through lumens 108, 110. Thereafter, limbs 62d, 64d are simply lifted through slots 112, 114 to remove the fully-threaded filaments from the device 100. One or more additional such tubes can be formed and utilized as desired. Also, the tubes 102, 104 can be formed as "C" or "U" shapes in cross-section, with wider slots than illustrated.

There are a number of other configurations of snare assemblies according to the present invention which have one or more adjustable-length noose support stems or limbs that enable the noose to be retracted as desired toward an anchor. These configurations provide an additional level of control over the final filament positions and tensions. Snare assembly 120, FIG. 15, has a noose 124 formed at one end of a first filament 122 with a stem section 126 extending into anchor 130 to pass through ratchet-like one-way gate or clamping mechanism 132. The remainder of filament 122 serves as a limb 128, also referred to as a stem tail. Some examples of one-way mechanisms are disclosed in U.S. Pat. No. 5,702, 397 by Goble et al., for example, which allow filament movement in only one direction.

Figure 15:
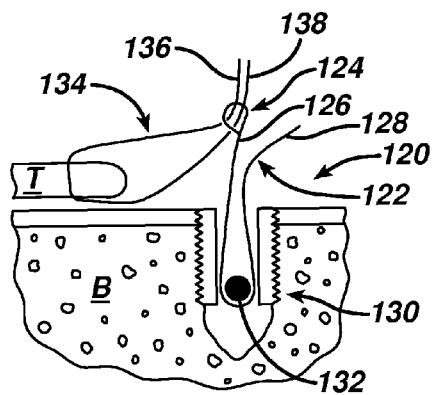
FIGS. 15-19 illustrate different snare assemblies with retractable-noose configurations according to the present invention.

As illustrated in FIG. 15, anchor 130 is fixated in bone B. A second filament 134 is passed through tissue T and has free limbs 136 and 138 passed through noose 124, initially positioned outside of a joint space surrounding tissue T. Limb 128, also positioned outside of the joint space, is pulled to retract noose 124 toward mechanism 132. Typically, the noose 124 is collapsed, limb 128 is trimmed, and then a procedure similar to that illustrated for FIGS. 7-10 above is utilized.

Figure 16:
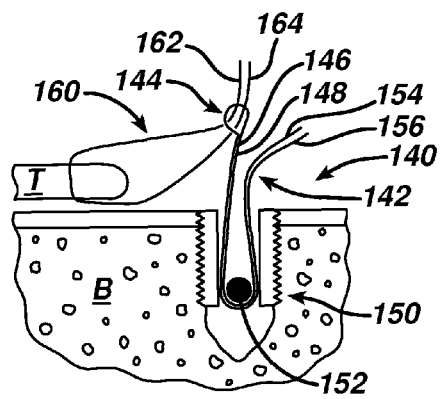

Snare assembly 140, FIG. 16, has first filament 140 having a noose 144 tied with two stem limbs 146 and 148 extending into anchor 150. In this construction, anchor post 152 serves as a filament engagement feature to slidably attach filament 140 to anchor 150. Filament stem tail limbs 154, 156 extend out of a joint space, together with noose 144 in an initial configuration. Second filament 160 is passed through tissue T and then free limbs 162, 164 are passed through noose 144 outside of the joint space.

Figure 16A:
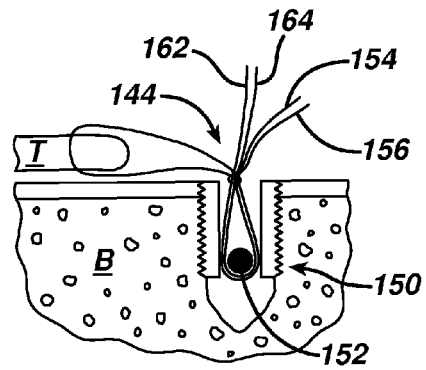

In the procedure illustrated in FIG. 16A, limbs 154 and 156 of first filament 142 are also passed through noose 144 and then pulled to collapse noose 144 about all four limbs 154, 156, 162 and 164 and to retract noose 144 toward filament engagement post 152. One or more sliding knots are tied on limb pair 154, 156 of the stem tails to adjust the proximity of noose 144 to the anchor 150 and then a simple knot is tied on free limbs 162, 164 to adjust final tension on tissue T, although other combinations and permutations can be utilized within the scope of the present invention. Typically, the sliding knots are finished with one or more half hitches to "seal" or complete the fixation.

Figure 17:
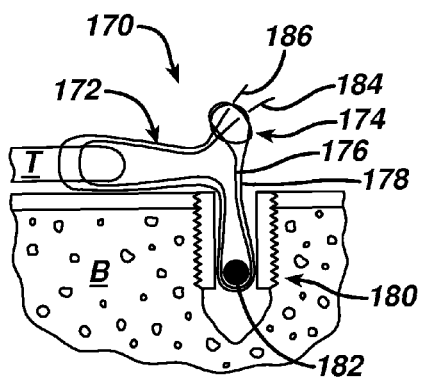

Snare assembly 170, FIG. 17, utilizes a single filament 172 both to secure noose 174 to anchor 180 and to tension tissue T. Stem limbs 176, 178 pass into anchor 12 and slidably around filament engagement post 182 to emerge from anchor 180 as tail limbs 184, 186 which are initially kept out of the joint space, along with noose 174, when anchor 180 is fixated in bone B. In some constructions, anchor post 182 is an eyelet or a pulley pin. Free tail limbs 184, 186 are passed through tissue T, in the same or different places or regions, and then through noose 174. Noose 174 is collapsed and pulled into the joint space by applying light tension to one, or preferably both, of the tail limbs 184, 186. A simple stopper knot is tied between tail limbs 184, 186 and pressed against the noose 174 while tensioning the limbs 184, 186 to place a desired amount of tension on tissue T. The fixation is finalized by placing one or more half hitches against the stopper knot at noose 174.

Figure 18:
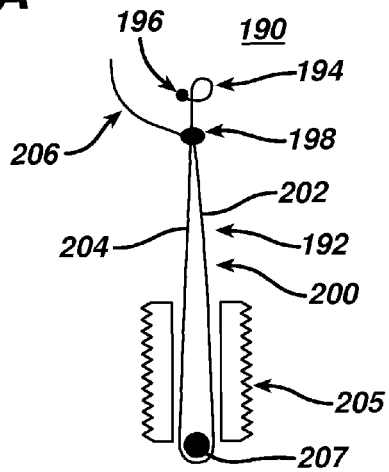

Snare assembly 190, FIG. 18, has functional similarities to snare assembly 120, FIG. 15, but achieves ratchet-like noose retraction without one-way gate or clamping mechanisms. Filament 192, FIG. 18, has a noose 194 with a stopper knot 196 at its terminal end to prevent pull-through and to resist fraying. A sliding knot 198 enables loop 200, having loop limbs 202 and 204, to be shortened toward anchor 205 when post limb 206 is pulled. Loop 200 passes around anchor saddle or post 207. This and other adjustable loop, sliding knot configurations are described in more detail below in relation to FIGS. 21-27.

Figure 19:
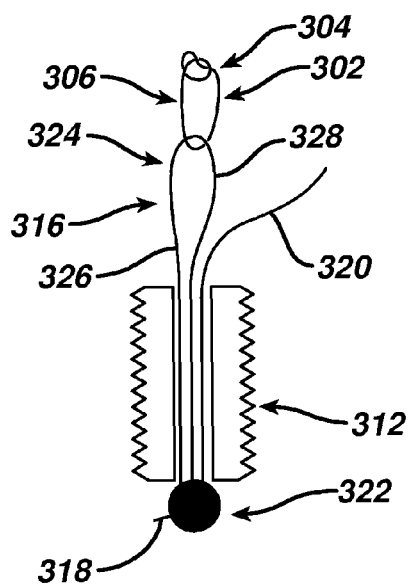

Snare assembly 310, FIG. 19, includes a first filament 302 with a noose 304 and a loop 306 which is fixed in length, the overall length of filament 302 being subject to full collapse of noose 304. A second filament 316 has a terminal end 318, a sliding knot 322 retained at the distal end of anchor 312, a post limb 320, and an adjustable loop 324 formed by limbs 326, 328. This configuration is described in more detail below in relation to FIG. 28.

Figure 20:
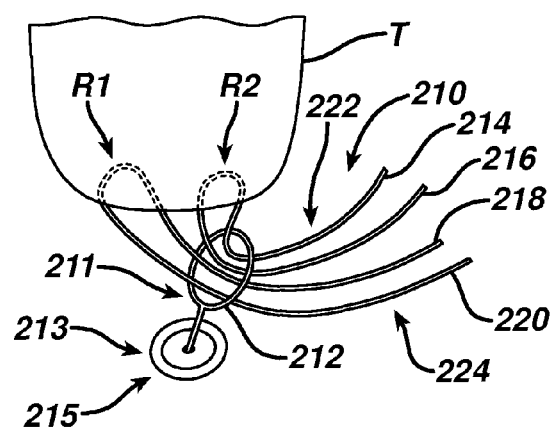
FIG. 20 is a schematic top view of multiple filaments that are passed through a single noose of a snare assembly according to the present invention.

While most of the embodiments herein have been described in relation to securing one or two filament limbs passed through a single place or region in a tissue T, this is not a limitation of the invention. Snare assembly 210, FIG. 20, has a first filament 211 with a noose 212 through which pass free limbs 214, 216 and 218, 220 of second and third filaments 222 and 224, respectively. Noose 212 is engaged by stem 213 with anchor 215. Filaments 222 and 224 pass through tissue regions R1 and R2, respectively. Multiple regions of a tissue, and potentially multiple types of sutures or other filaments, can thereby be secured using a single snare assembly according to the present invention.

Figure 21:
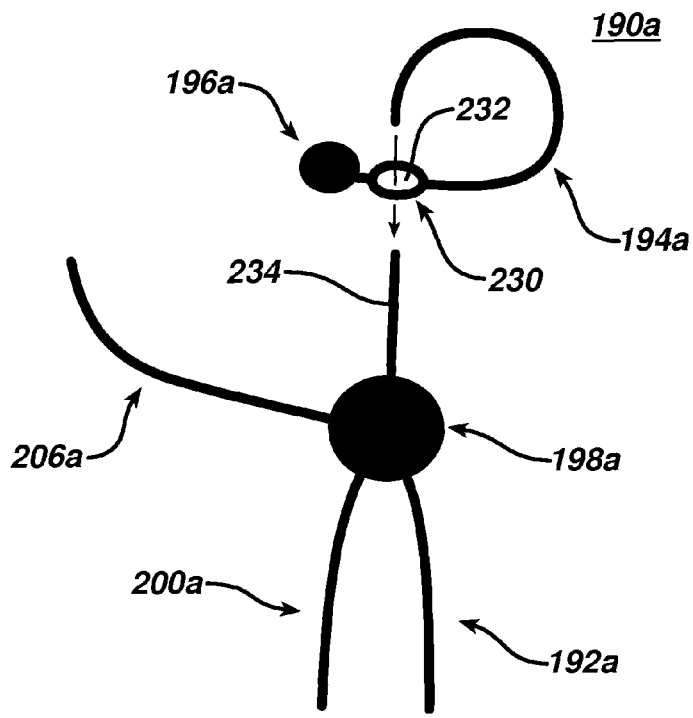
FIG. 21 is an enlarged view of one construction of the configuration shown in FIG. 18.

One arrangement of the filament 192 for snare assembly 190, FIG. 18, is illustrated in FIG. 21 for snare assembly 190a. Noose 194a is formed merely by creating opening 232 in region 230 of filament 192a and passing filament 192a through itself. Loop 200a and sliding knot 198a are formed thereafter on post limb 206a. In this arrangement, any tension applied on stem 234, such as by pulling post limb 206a, not only collapses noose 194a to strangulate objects passing through noose 194a, but also binds the portion of filament 192a passing through opening 232 upon itself. In other arrangements, a half hitch or other simple knot is tied at filament region 230, and filament 192a is then looped through that simple knot. Stopper knot 196a such as a simple half hitch will prevent the terminal end from fraying or opening up, especially if a braided filament such as Orthocord™ suture is utilized for filament 192a.

An example of steps for manufacturing snare assembly 190, FIG. 18, utilizing suture as filament 192 is as follows. Tie stopper knot 196 and trim the tail of the terminal end. Loop the suture and pass it through itself in close proximity to the stopper knot 196 to achieve the noose arrangement illustrated in FIG. 21, or tie a second half hitch in close proximity to the stopper knot and pass the suture through the half hitch to create the noose 194, FIG. 18. A thin mandrel or other object such as a pin may be placed through noose 194 to maintain patency. Sliding knot 198, such as a bunt line half hitch knot, is tied in close proximity to the noose 194 and the suture is placed in sliding engagement with feature 207 of anchor 205. Sliding knot 198 is then dressed or finalized as desired.

Conventionally, rotator cuff lateral row fixation involves spanning a suture bridge from medial anchors. Sutures are fixated with knotted or knotless anchors at the lateral row. Unthreaded anchors suffer more often than threaded anchors from anchor pull out, and suture slippage may occur at relatively low loads in many conventional procedures regardless of anchor type.

Figure 22:
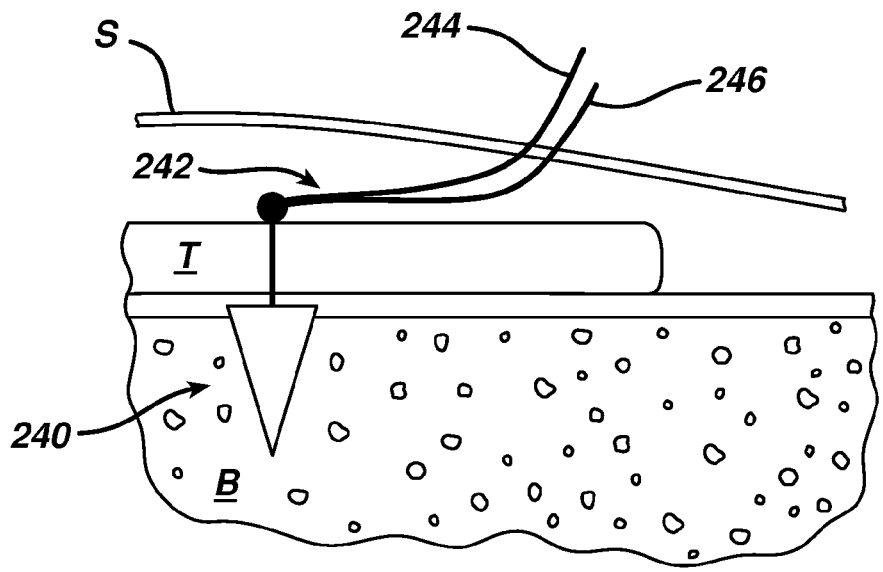
FIGS. 22-27 are schematic side views of the snare assembly of FIG. 18 utilized with another anchor placed through tissue to be repaired.
Figure 23:
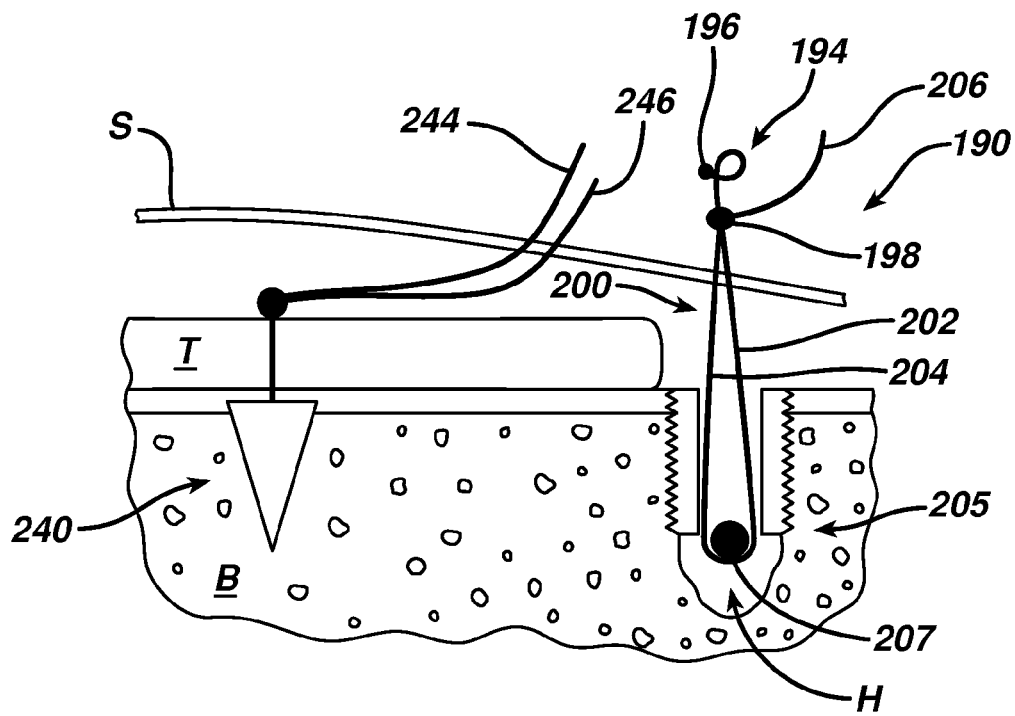

A presently preferred technique for rotator cuff double row repair is illustrated in FIGS. 22-27 utilizing the snare assembly of FIG. 18. Medial row anchor 240, FIG. 22, is shown already embedded in bone B having cuff tissue T fixated at the medial row with suture 242. Preferably, a threaded anchor is utilized for anchor 240, and may be the same type of anchor as anchor 205. Free suture limbs 244 and 246 are retracted out of the joint space, shown in FIG. 22 as extending beyond skin S. Threaded anchor 205, FIG. 23 is then placed as a lateral row anchor in hole H independently of the medial row fixation. At this stage, collapsible loop 200 is long enough to enable sliding knot 198 and noose loop 194 to extend out of the joint space.

Figure 24:
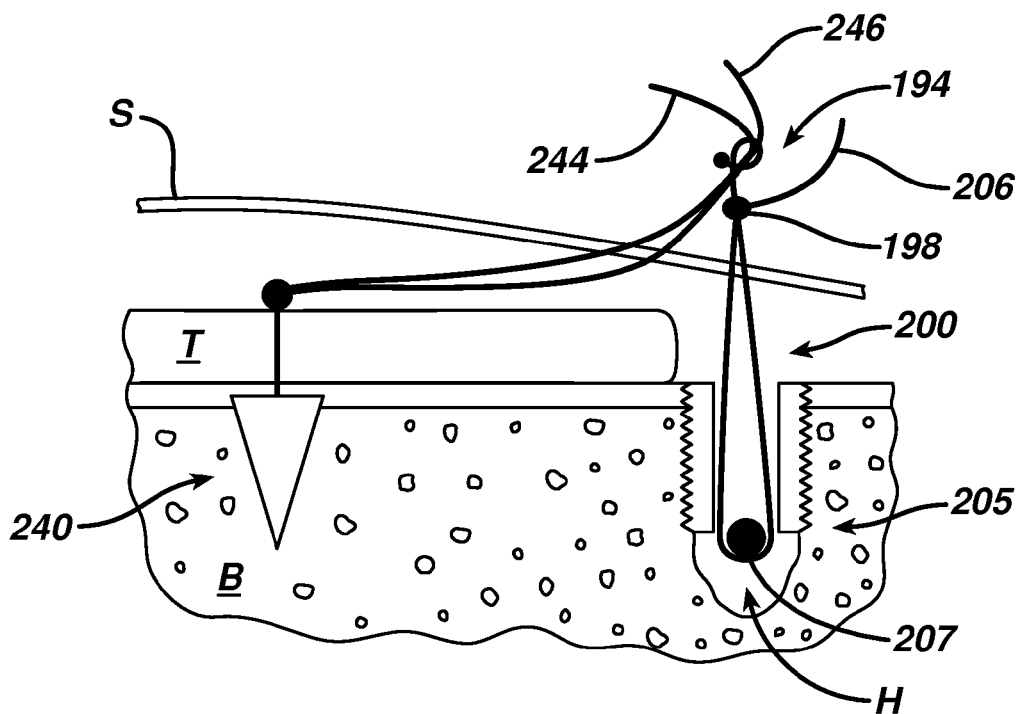
Figure 25:
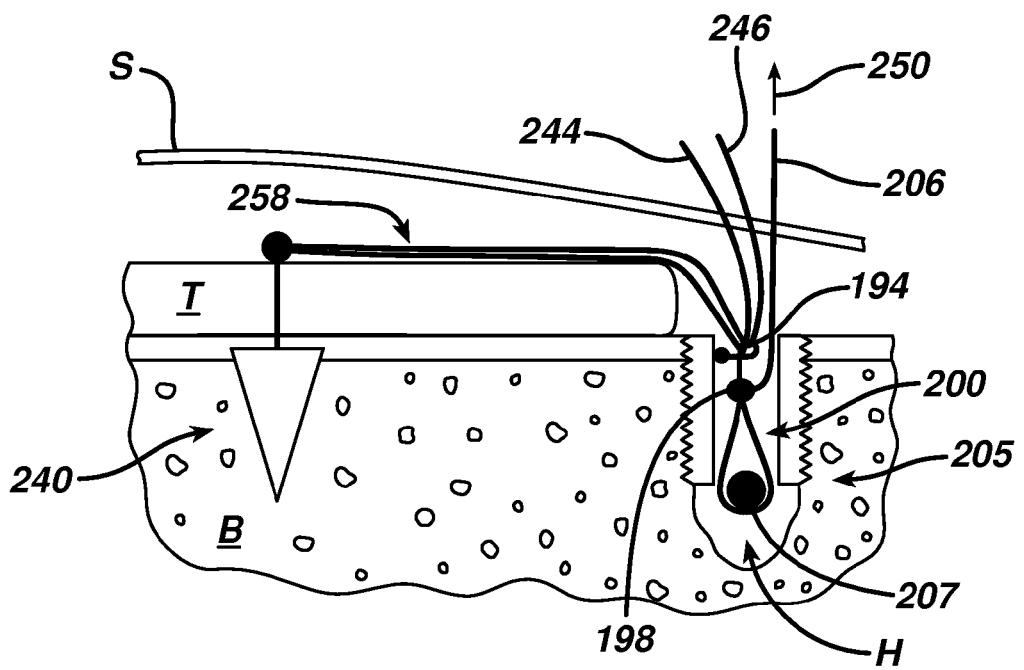

Suture limbs 244, 246 from the medial row are then passed through noose 194, FIG. 24, preferably utilizing one of the threader devices described above. Any tension on suture limbs 244, 246 will collapse noose 194 around them. The size of the threader tube may be selected to limit the migration of noose 194 from sliding knot 198. Post limb 206 is then tensioned, FIG. 25, in the proximal direction indicated by arrow 250 to retract sliding knot 198 into or in close proximity to anchor 205 and to place initial tension on suture bridge 258.

Figure 26:
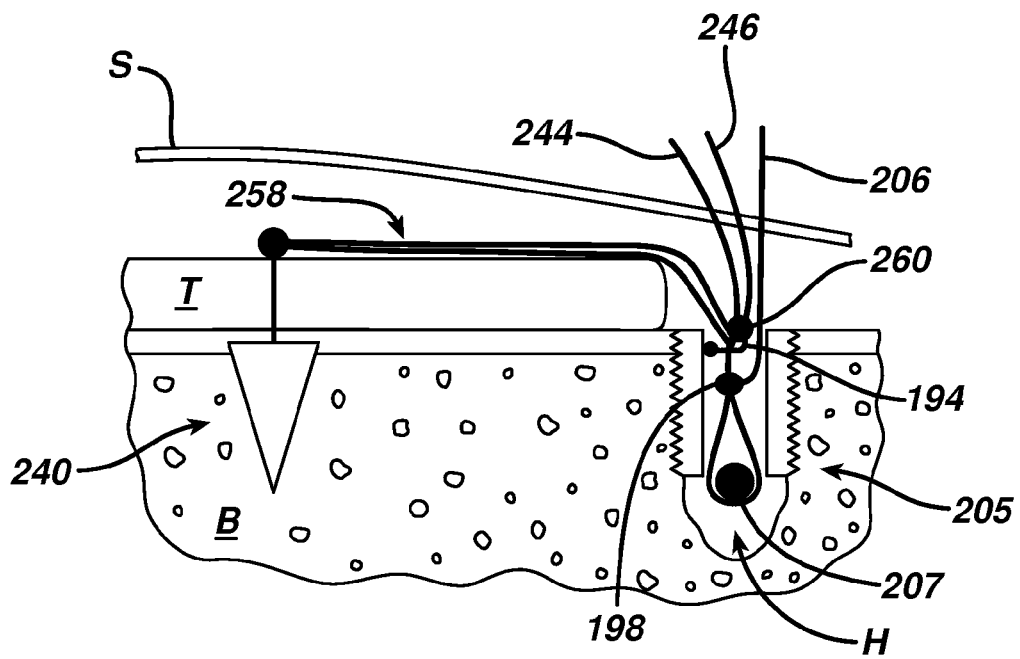
Figure 27:
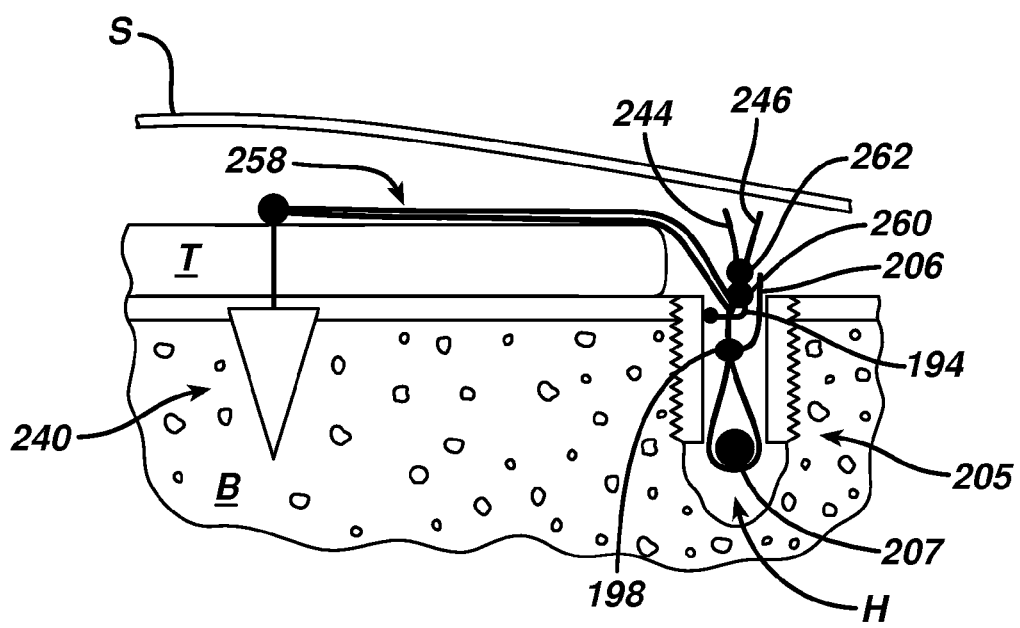

A simple knot such as a half hitch is then tied between suture limbs 244, 246 and pushed down against noose 194, FIG. 26, as sliding knot 260 while limbs 244 and 246 are pulled to further tension suture bridge 258 as desired. As second or more half hitches 262, FIG. 27, are added after suture bridge 258 has been properly tensioned to permanently lock the repair and the ends of suture limbs 244 and 246 are trimmed. Because a single noose can handle multiple pairs of sutures as described above in relation to FIG. 20, additional suture bridges can be secured from multiple medial anchors as desired.

Figure 28:
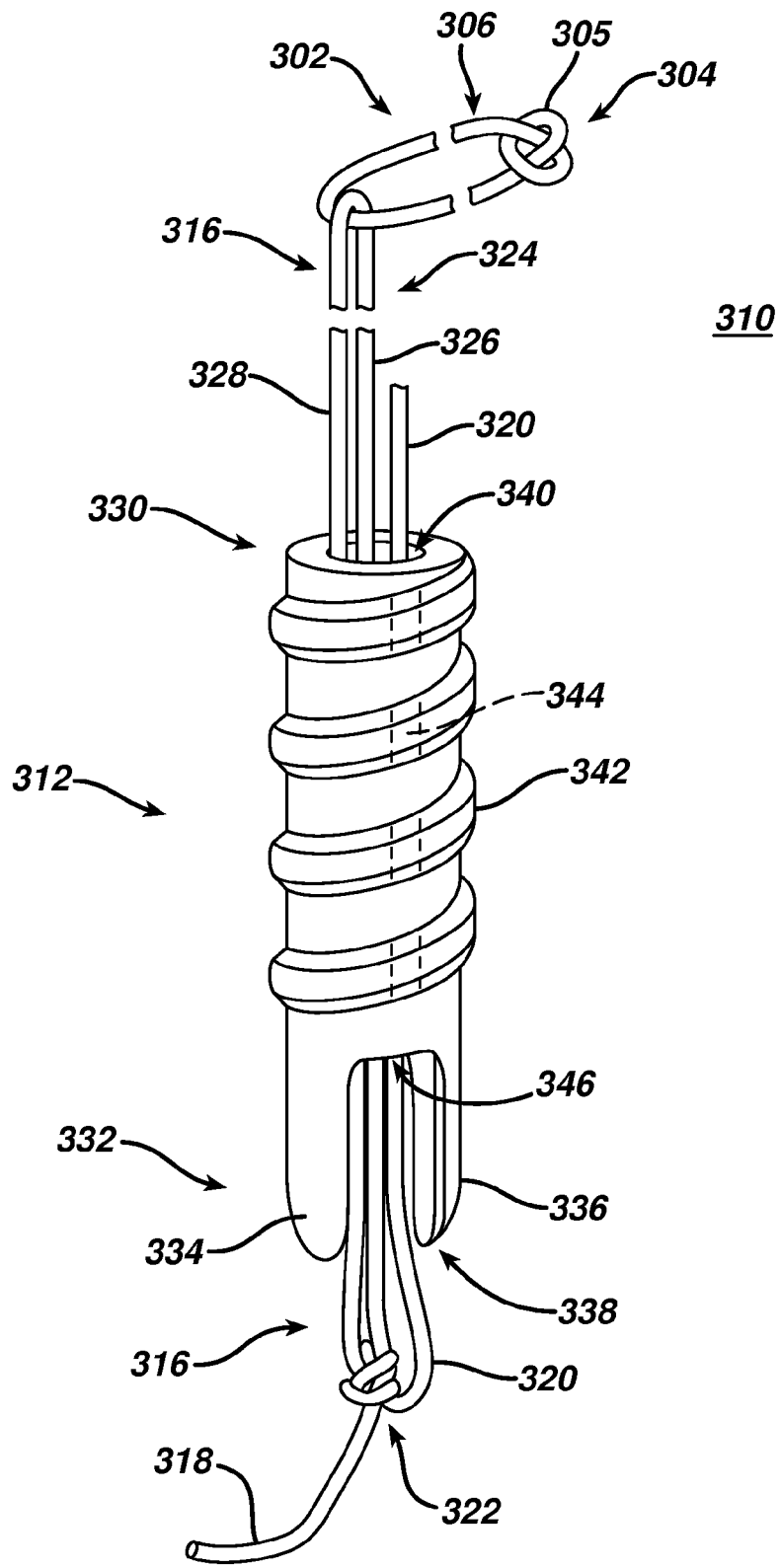
FIG. 28 is a perspective view of a snare assembly according to the present invention having a cannulated suture anchor.

Adjustable suture snare assembly 310, FIG. 28, has a suture anchor 312 and a closed, fixed-length loop 306 of a first material 302, which has a noose 304 tied at one end. A half hitch "pretzel"-like knot 305 is shown in this construction; another construction having a unitary fixed loop is disclosed in U.S. patent application Ser. No. 12/977,146 (Hernandez et al.), which is incorporated herein by reference. Loop 306 is captured by, in other words, is connected to, a second filament 316 having a terminal end 318, a post limb 320, a sliding bunt line half hitch knot 322, and an adjustable loop 324 with loop limbs 326 and 328. Second filament 316 may be considered as part of an adjustable filament engagement feature of anchor 12, because filament 316 connects noose 304 to anchor 12. In one construction, suture anchor 312 is similar to the cannulated suture anchor disclosed by Cauldwell et al. in U.S. Patent Application Publication No. 2008/0147063, incorporated herein by reference. In anchor systems utilized according to this sliding knot configuration of the present invention, however, it is not necessary to have a post-like suture-engaging member or other occluding element over which one or more sutures or suture limbs pass to serve as a restriction to proximal movement; in many constructions, it is sufficient to have a restricted opening 346 to prevent withdrawal of knot 322.

Suture anchor 312 has a proximal end 330 and a distal end 332 with opposed distal arms 334 and 336 defining cut-out 338 between them. Passage 340 is an inner lumen which runs from proximal end 330 to distal cut-out 338. Although knot 322 is shown extending beyond cut-out 338 in FIG. 28 for purposes of illustration, knot 322 preferably is seated against restricted opening 346 between arms 334 and 336, or otherwise maintained at the distal end 332 by a cavity or other feature, during insertion of snare assembly 310 into a patient to minimize interference by the knot 322 with the bone-engaging feature 342, or other exterior surface of anchor 312, and the bone in which suture anchor 312 is fixated.

One or more bone-engaging features 342, such as the helical thread illustrated in FIG. 28 or other features such as teeth, ridges, or other protrusions, are formed on the exterior of anchor 312 to enhance fixation in bone. Threads such as found on the Healix™ anchor available from DePuy Mitek Inc. are desirable. In another construction, the suture anchor rotates to toggle into bone at its proximal end to minimize withdrawal. In a number of constructions, a hole is formed in bone prior to anchor insertion; in other constructions, a suture anchor is inserted directly into bone. Further, one or more passages or channels may be formed on the exterior of the suture anchor, such as channel 344 illustrated in phantom, FIG. 28, traversing bone-engaging element 342.

It is a matter of surgeon preference whether a terminal end 318 is kept at a length sufficient to lie against the exterior of at least one bone-engaging feature 342 to be trapped against bone during insertion, or is trimmed to a shorter length. Further, a restriction such as restricted opening may be defined at least in part by engagement with bone when anchor 312 is fixated in bone to prevent knot 322 from moving with post limb 320 when tension is applied to post limb 320.

One or more such distal extensions or other protrusions may be provided, similar in some constructions to Cauldwell et al. cited above or to U.S. Pat. No. 7,381,213 by Lizardi, also incorporated herein by reference. In yet other constructions, a cylindrical or otherwise circumferential cavity, bowl or countersink feature is provided at the distal end of the anchor to seat the knot 322 during insertion and fixation.

Slidable knot 322 has been described as a bunt line half hitch knot in some constructions, but other suitable knots will be readily apparent to those of ordinary skill in the suture tying art after reviewing the present invention. The term "slidable" as used herein is intended to include slidable, lockable knots as well as slidable knots, such as those described in the Arthroscopic Knot Tying Manual (2005) available from DePuy Mitek, as well as the slidable, lockable knot by Wenstrom, Jr. in U.S. Pat. No. 6,767,037.

Several improvements according to the present invention are illustrated in FIGS. 29-50. A filament 400, FIG. 29, has a noose 402 and noose limbs 404 and 406. Noose 402 defines a central opening 408 and secondary openings 410 and 412 formed from a half hitch plus one additional throw of limb 406 through central opening 408. A flexible sleeve 414 is shown in phantom encapsulating some of limbs 404 and 406 in certain constructions, as described in more detail below.

Figure 29:
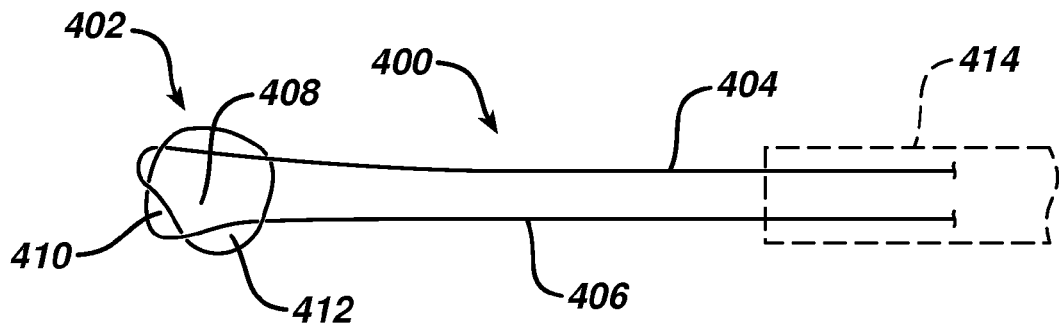
FIG. 29 is a schematic view of a filament having a snare formed as a half hitch plus an additional throw with first and second noose filament limbs extending therefrom, and one embodiment of a sleeve, indicated in phantom, according to the present invention covering some of the first and second filament limbs.
Figure 30:
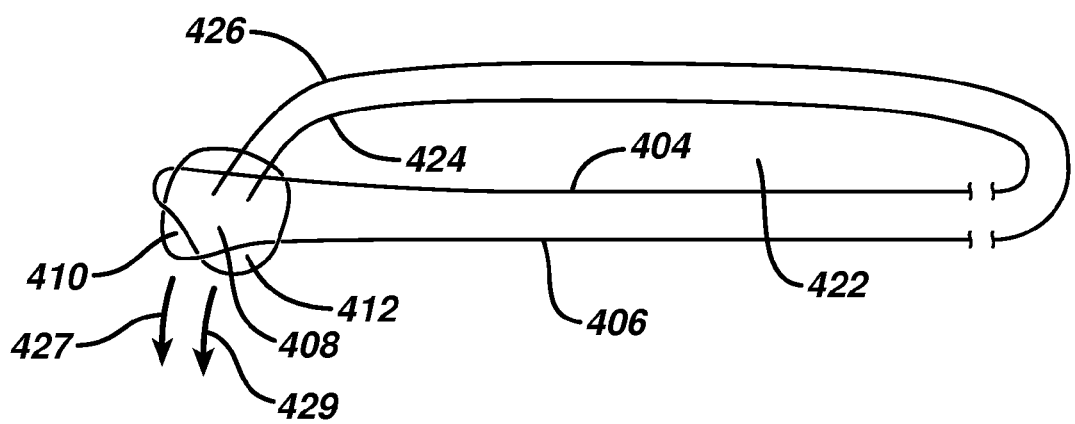
FIGS. 30 and 31 are sequential views of the filament of FIG. 29 with the free filament limbs being passed through the noose to form a cinch noose, with a distal portion of a sleeve illustrated in FIG. 31.
Figure 31:
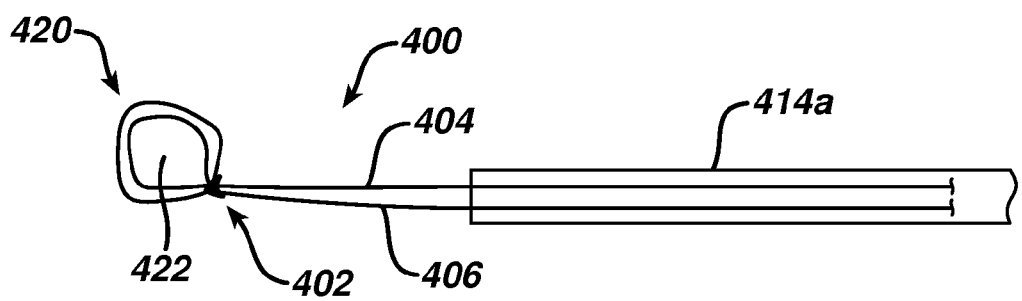

FIGS. 30-31 illustrate the formation of a cinch noose 420, also referred to as an improved cinch noose construct, having an opening 422. The ends of free filament limbs 424 and 426 of filament 400 are passed through central opening 408, as represented by arrows 427 and 429 in FIG. 30, which draws noose limbs 424 and 426 therethrough. Noose 402 is then tightened, FIG. 31, to form a slidable knot for cinch noose 420. Alternatively, if a sleeve 414, FIG. 29, or sleeve 414a, FIG. 31, is not utilized, or if such sleeve is removed after being passed through tissue to be tensioned, then one or both of free limbs 424, 426 can be passed through one or both of openings 410, 412. One technique for utilizing improved cinch noose 420 is described below regarding FIGS. 34-40.

Figure 32:
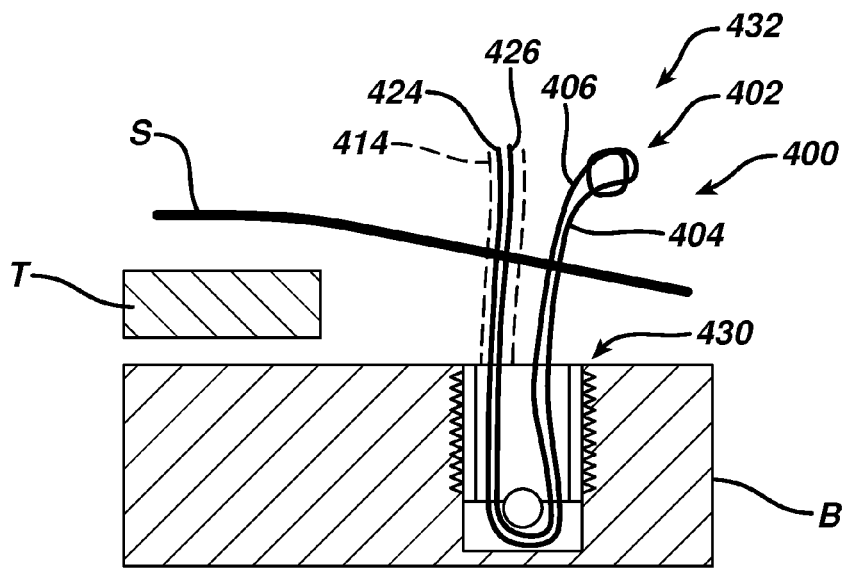
FIG. 32 is a schematic side view of the filament and sleeve combination of FIG. 29 implanted in a patient with an anchor.

Filament 400 with noose 402, FIG. 29, is shown in FIG. 32 slidably connected with anchor 430 as a snare assembly 432, after placement through skin S into bone B of a patient. Sleeve 414 is positioned over and encapsulates the entire portion of first and second free limbs 424, 426, down substantially to, but not into, anchor 430 in this construction.

It is a realization of the present invention that joining together at least the free filament limbs improves suture management and reduces the possibility of suture entanglement or damage by instruments, especially when passed through a cannula. For example, a surgeon or other user need only grasp and pass one sleeve 414 through noose 402 to thereby manipulate free filament limbs 424, 426 as a single unit. Additional convenience can be provided by perceptible indicators on one or more sleeves such as different markings, colors, diameters, braid or design patterns, or other tactile or visual indicia, especially if multiple tissue attachments or anchors are utilized, such as described above in relation to FIG. 20. Preferably, the sleeves are removed and discarded after the filaments have been manipulated, as described below, so the perceptible indicators do not need to meet long-term implantation requirements.

Figure 33:
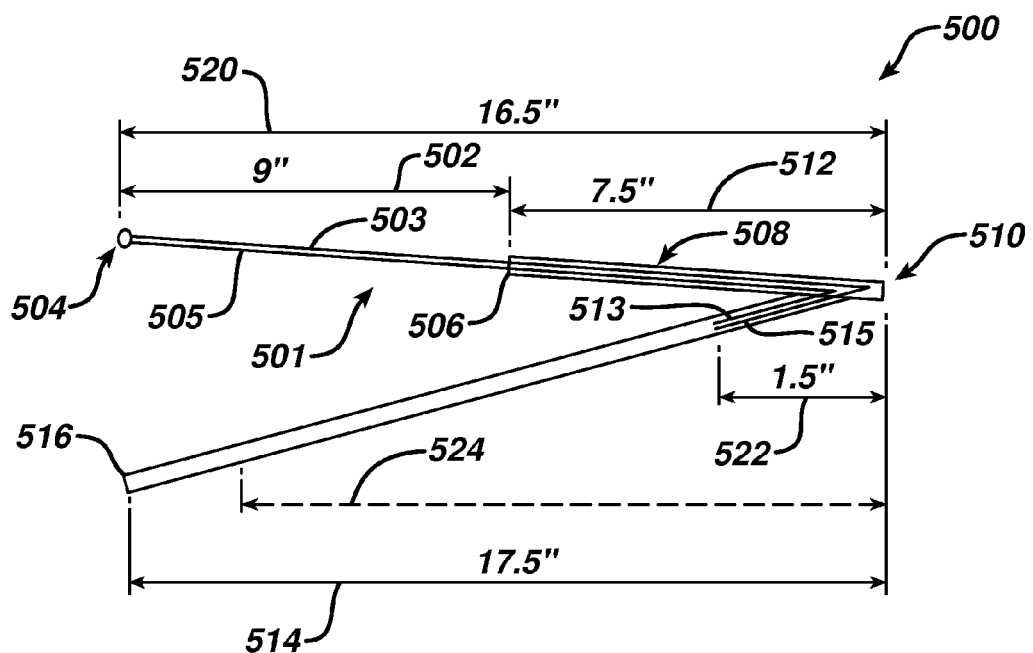
FIG. 33 is a sketch of calculations for the relative lengths and positions of filament limbs relative to a sleeve for certain embodiments according to the present invention.
Figure 34:
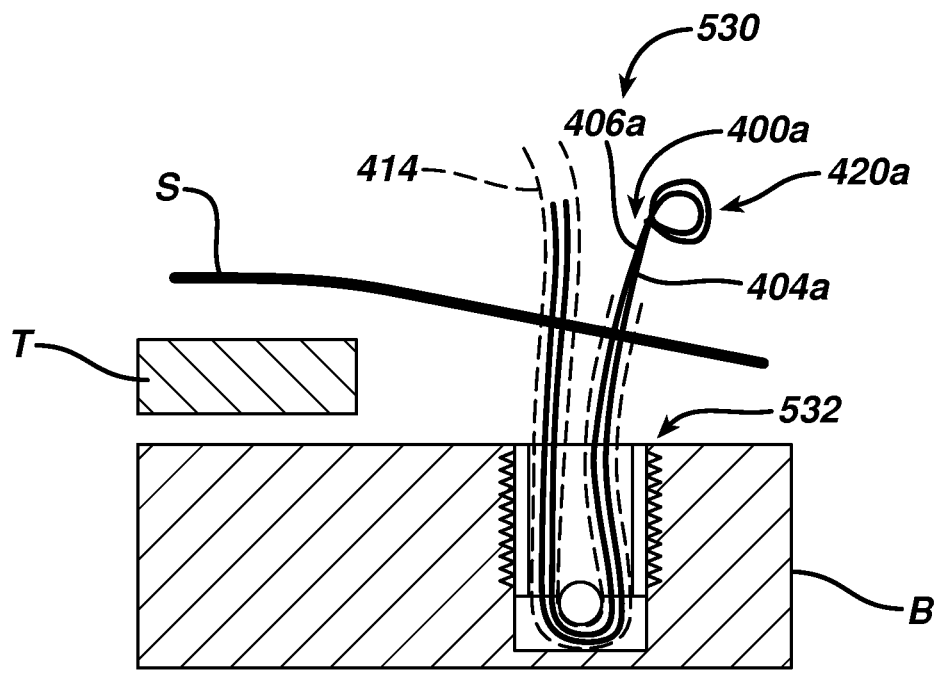
FIGS. 34-40 are schematic side views illustrating capture and tensioning of tissue utilizing another embodiment of sleeve and filament snare assembly according to the present invention.

One technique for calculating the relative lengths of filament 501 and sleeve 508 is illustrated in FIG. 33 for snare assembly 500 according to the present invention. A first factor is the distance, represented by arrow 502, between noose 504, in a substantially collapsed or reduced condition, and the distal end 506 of sleeve 508 over noose limbs 503 and 505. One goal is to have distal end 506 accessible outside of a cannula after tissue is tensioned to enable latching or snagging of distal end 506 by a knot pusher or grasper to facilitate removal of sleeve 508, as described in more detail below for other sleeves. Typical cannula lengths for hip and shoulder surgeries are between four to six inches, and the cannulas are typically placed approximately one-half inch from bone. The length of anchor 510 is included in the calculation.

For some constructions prior to implantation in a patient, sleeve 508 is twenty five inches in total length, with seven and one-half inches extending from the filament engagement feature of anchor 510 toward noose 504 as indicated by arrow 512, with seventeen and one-half inches, arrow 514, extending over and beyond free filament limbs 513 and 515 to proximal end 516 of sleeve 508. In one construction, filament 501 has a total length of thirty six inches, or a folded length of eighteen inches, with sixteen and one-half inches, arrow 520, extending from noose 504 to anchor 510, and one and one-half inches, arrow 522, as free limbs 513 and 515. In another construction wherein filament 501 has a total length of sixty six inches and a folded length of thirty three inches, free filament limbs 513, 515 extend sixteen and one-half inch as represented in phantom by arrow 524. In either construction, marks can be placed on the filament noose limbs 503, 505 nine inches from the center or middle, where noose 504 will be formed, to clearly indicate the proper positioning, arrows 502 and 512, of distal end 506 of the sleeve 508 over filament 501 during preparation of snare assembly 500 for implantation.

A technique for utilizing the improved cinch noose 420, FIG. 31, with a sleeve 414a is shown in FIGS. 34-40 for another embodiment, represented by snare assembly 530 according to the present invention. In this construction, the sleeve 414a, shown with dashed lines, is slid over filament 400a and then loaded through anchor 532 to cover all of free limbs 424a, 426a and at least some of noose limbs 404a, 406a, preferably covering all of noose limbs 404a, 406a as they emerge above a cannula (not shown) passing through skin S during initial implantation of anchor 532 in bone B, FIG. 34 to assist in suture management and protection.

Figure 35:
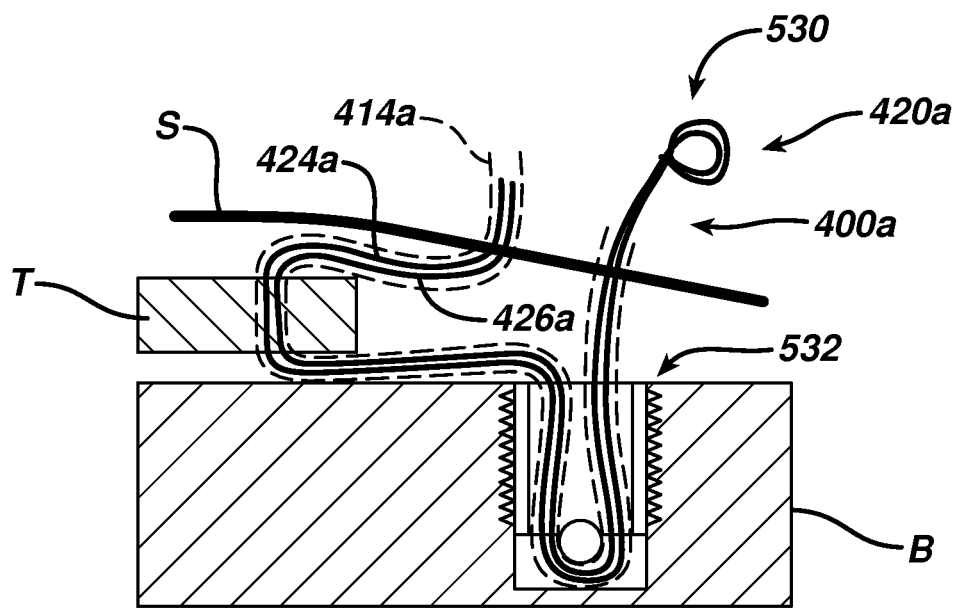
Figure 36:
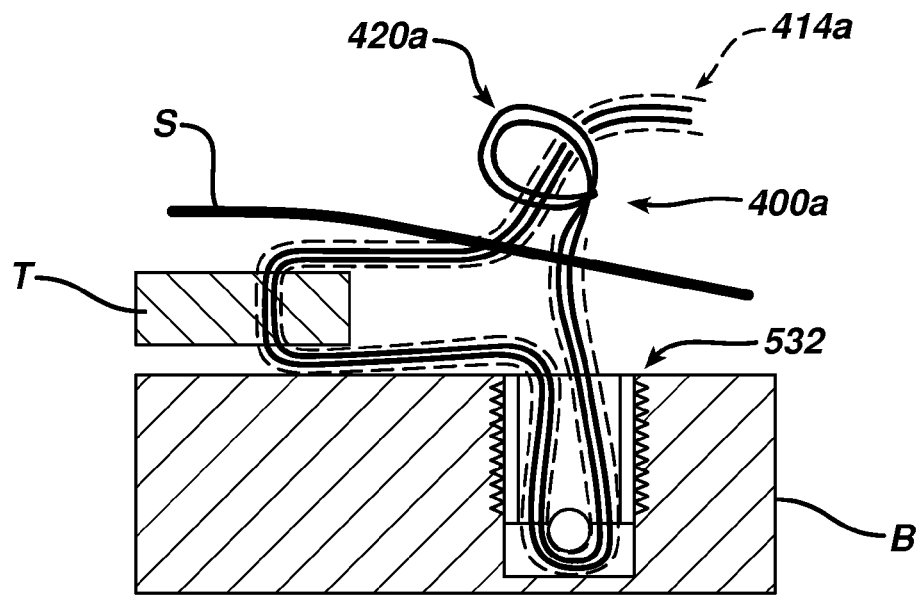
Figure 37:
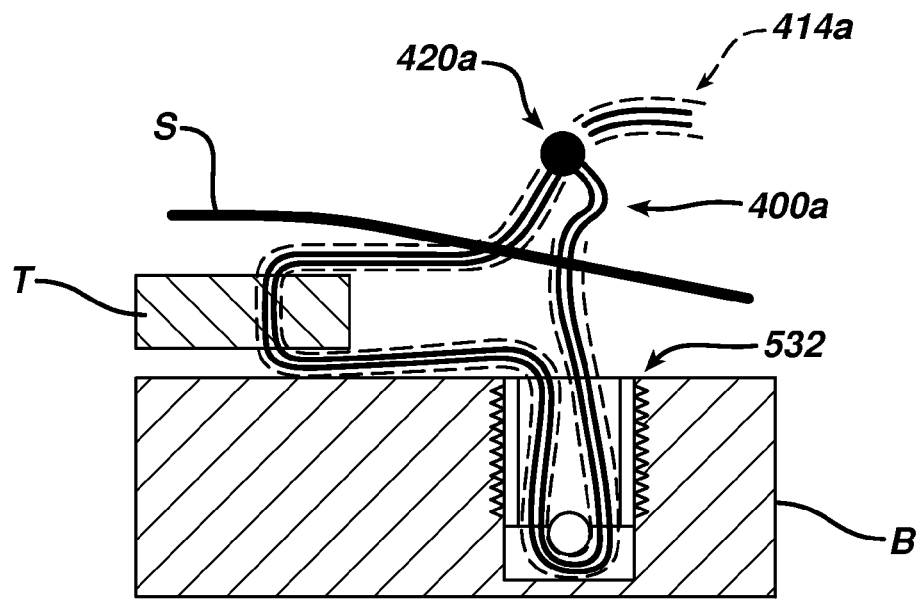
Figure 38:
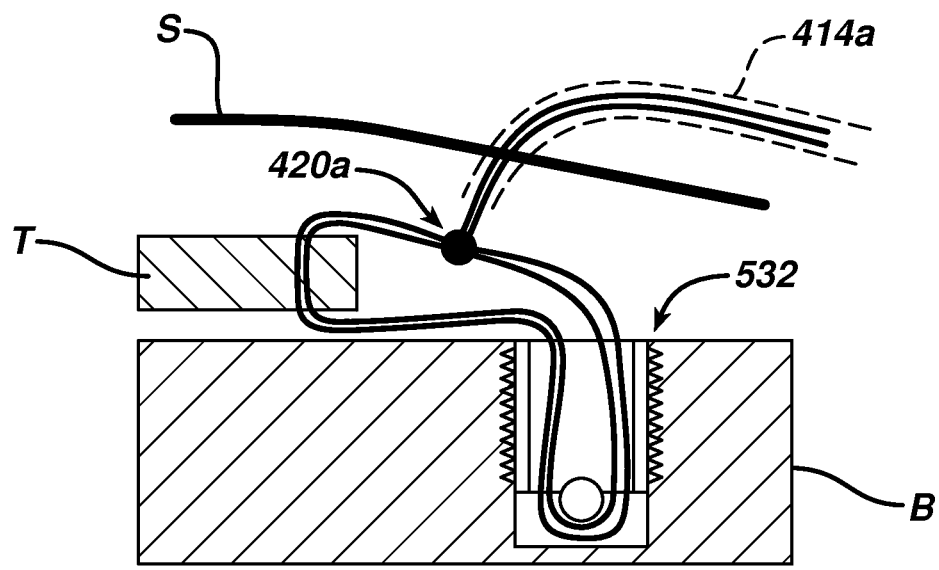
Figure 39:
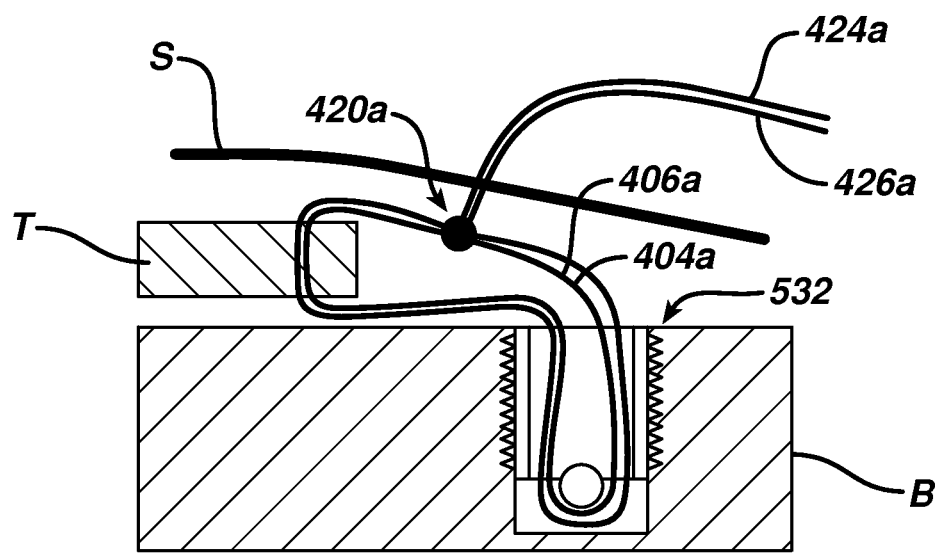
Figure 40:
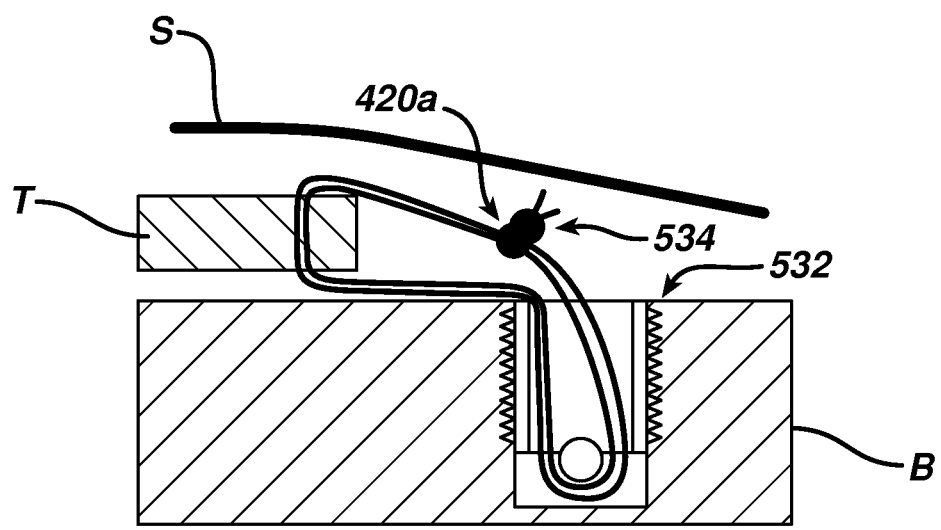
Figure 41:
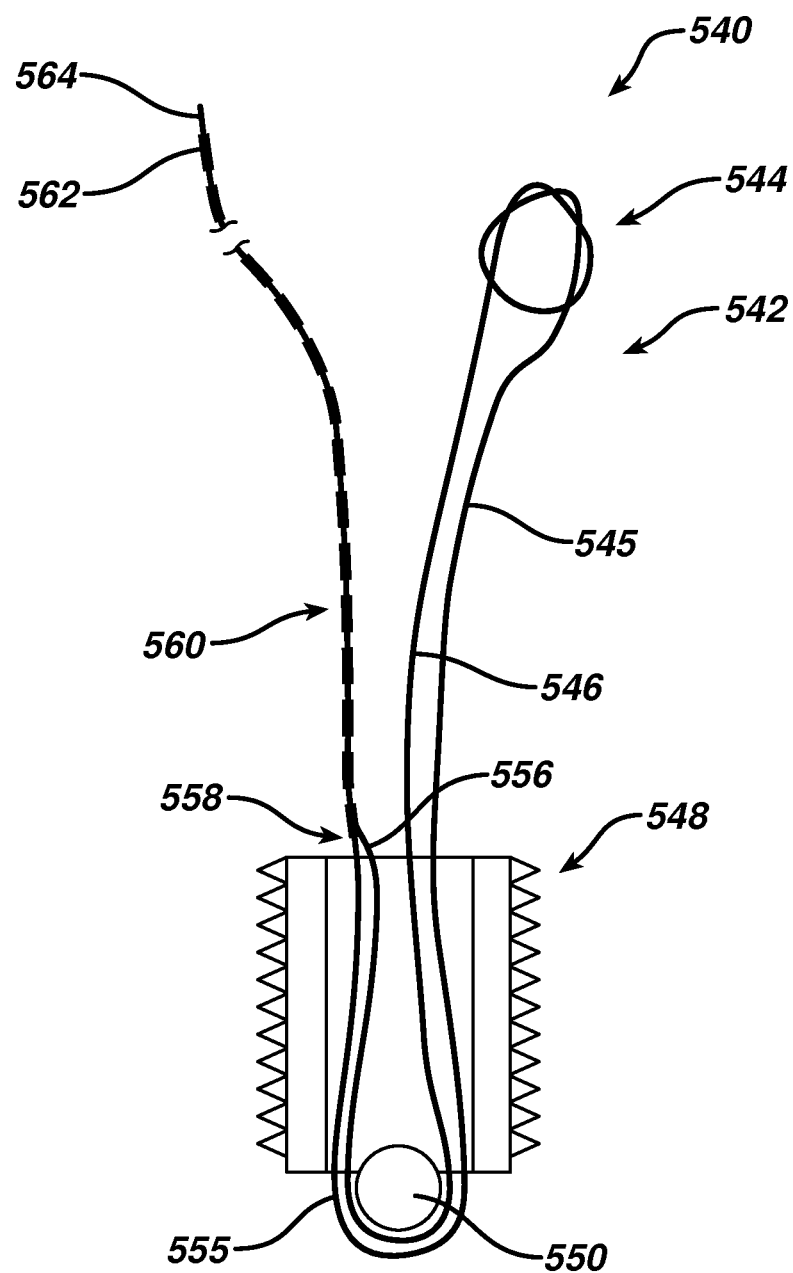
FIG. 41 is a schematic side view of yet another sleeve and filament snare assembly according to the present invention.

The proximal end of sleeve 414a is passed through tissue T, FIG. 35, and then passed through cinch noose 420a, FIG. 36. Alternatively, sleeve 414a can be removed after it is passed through noose 420a so that free limbs 424a and 426a can be passed directly through one or more openings in noose 420a. In either scenario for FIG. 36, the noose 420a is then dressed, that is, collapsed, FIG. 37, and then advanced near tissue T and tightened, FIG. 38. The sleeve 414a is then removed entirely, FIG. 39, and discarded according to standard procedures. The tissue repair is then finished with one or more half hitches 534 as desired, FIG. 40.

Materials for sleeves include braided sutures such as Ethibond™ size 0 suture or Orthocord™ size 2 suture, also referred to as Orthocord™ #2 suture, which is typically braided at sixty picks per inch. For use as a sleeve, a more relaxed braid of approximately thirty to forty picks per inch is preferred, more preferably about 36 picks per inch. If the sleeve material is formed about a core, preferably that core is removed to facilitate insertion of the filament limbs, which may themselves be formed of typical suture such as Orthocord™ #0 suture or #2 suture braided at sixty picks per inch.

In yet another sleeve embodiment according to the present invention, one of the free filament limbs itself serves as the sleeve. For the construction illustrated in FIG. 41, snare assembly 540 has a filament 542 of Orthocord™ #2 suture generally braided at sixty picks per inch with a noose 544 and noose limbs 545 and 546 that pass around filament engagement feature 550 of anchor 548. Noose limbs 545 and 546 become free filament limbs 555 and 556, respectively, extending proximally. At point 558, however, a proximal section of limb 555 is braided at fewer picks per unit length, preferably more than ten percent fewer, more preferably at least twenty five percent fewer, to serve as sleeve 560 extending to its proximal end 562. The other free filament limb 556 is threaded through sleeve 560 to emerge as proximal end 564 in this construction; in other constructions, the proximal end 564 lies wholly within sleeve 560.

Figure 42A:
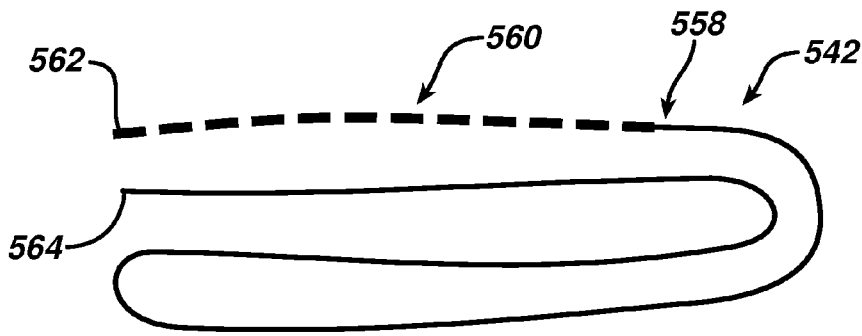
FIGS. 42-46 are schematic side views of capture and tensioning of tissue utilizing the assembly of FIG. 41.
Figure 42B:
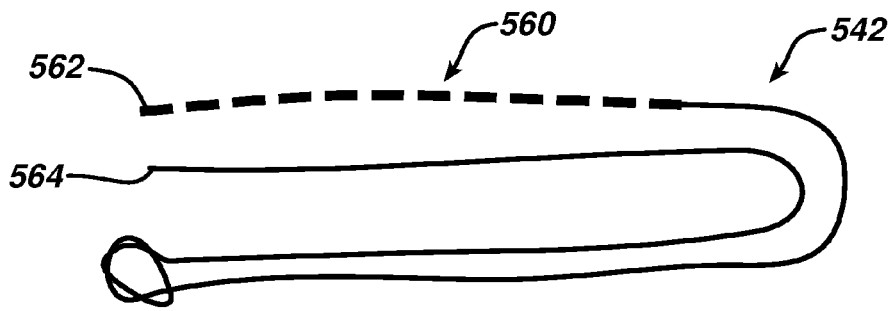
Figure 42C:
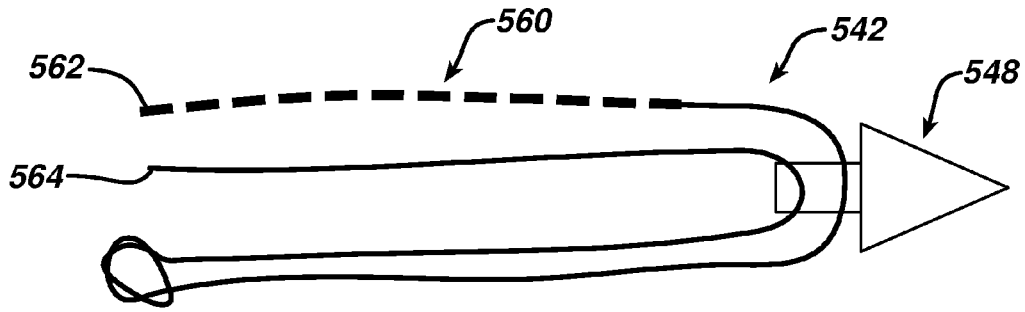
Figure 42D:
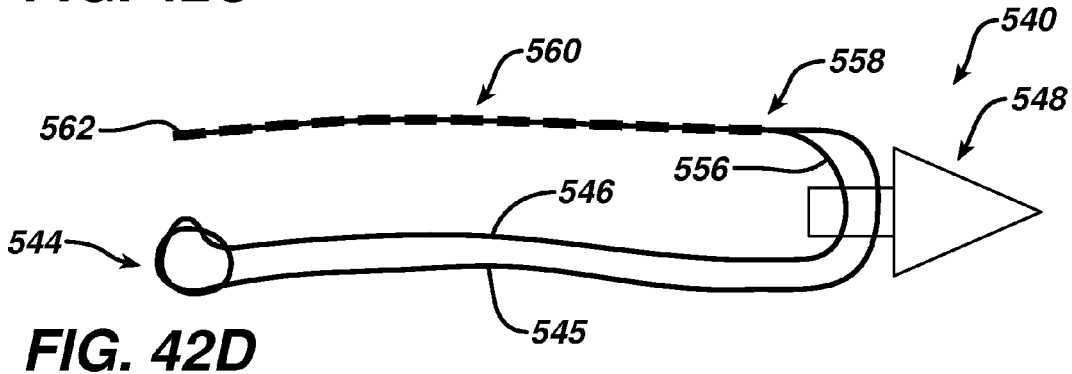

One technique for constructing snare assembly 540 is illustrated in FIGS. 42A-42D. Filament 542 is shown in FIG. 42A as initially manufactured with sleeve 560 being a section of suture formed with fewer picks per inch beginning at point 558 and extending to end 562, preferably reduced from the standard 60 picks per inch to 36 picks per inch in this construction. Noose 544 is then created, FIG. 42A, and then filament ends 562, 564 are threaded through anchor 548 as shown schematically in FIG. 42C. After a core element within sleeve section 560 has been removed, filament end 564 is then threaded within sleeve 560 using a needle-type insertion device to achieve snare assembly 540, FIG. 42D, with coaxial filament limbs in the sleeve section 560. The length of sleeve 560 is likely to decrease as its diameter is expanded by the insertion device.

Figure 43:
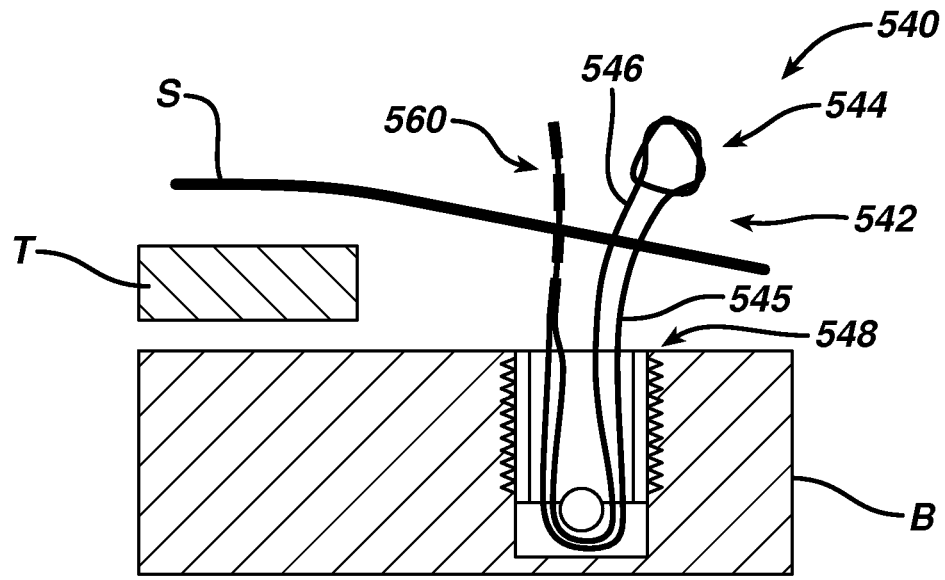
Figure 44:
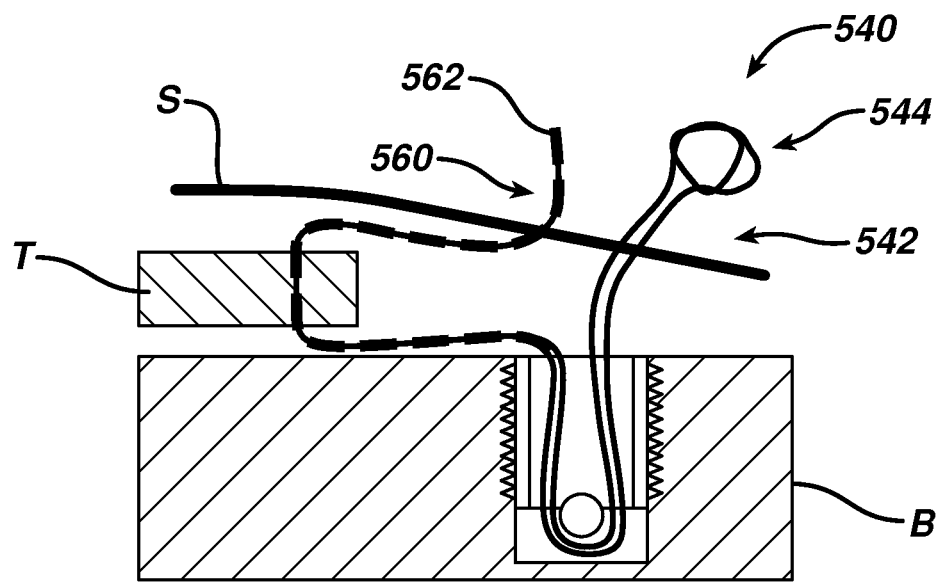
Figure 45:
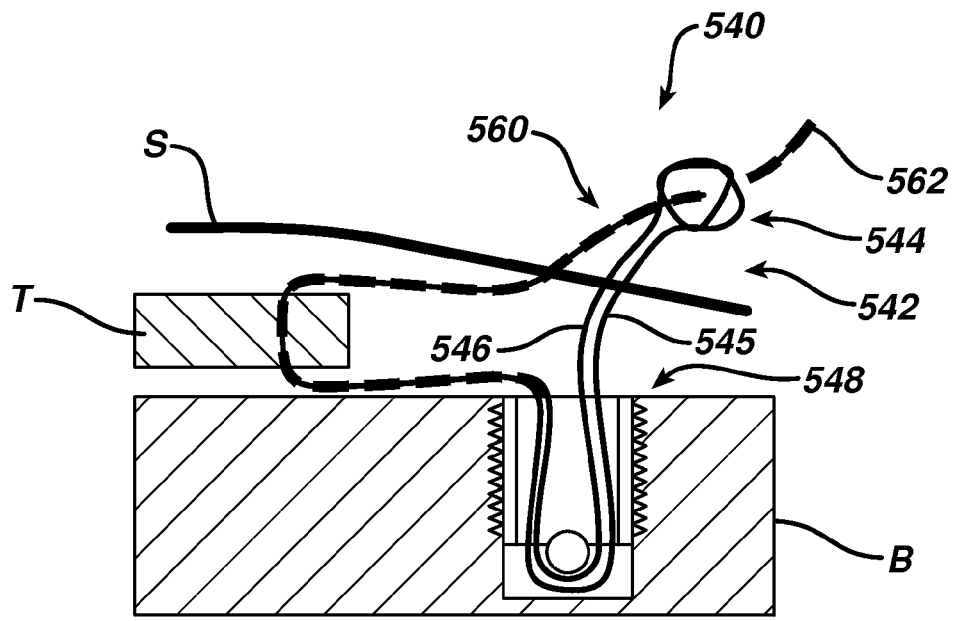
Figure 46:
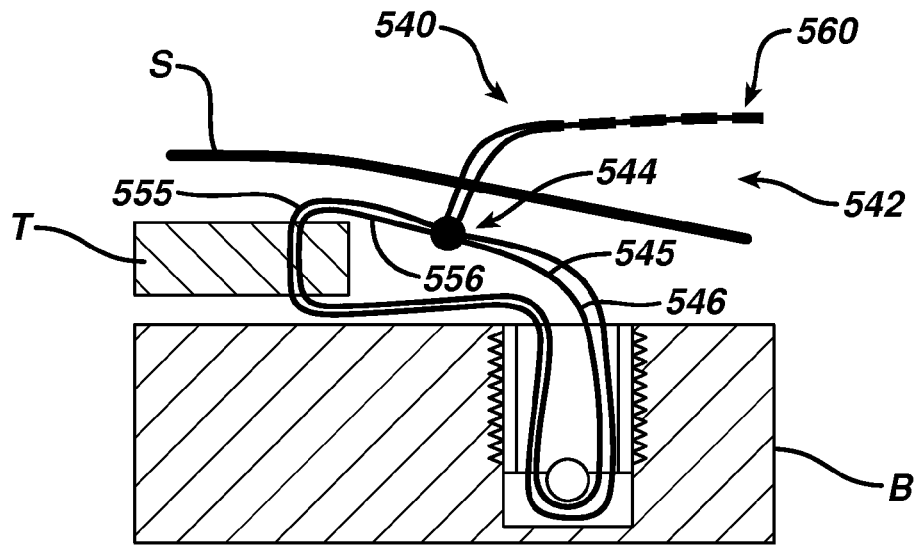

One procedure for utilizing snare assembly 540 is shown in FIGS. 43-45. Anchor 548 is inserted into bone B, FIG. 43, and then coaxial sleeve section 560 is passed through tissue T, FIG. 44, and then noose 544, FIG. 45. Noose 544 is then collapsed toward tissue T, FIG. 46, sleeve 560 is severed from filament 542, and then filament 542 is tied and cut as described above for other embodiments to finish fixation of tissue T. The excess portion of filament 542, including coaxial sleeve section 560, is discarded.

Figure 49:
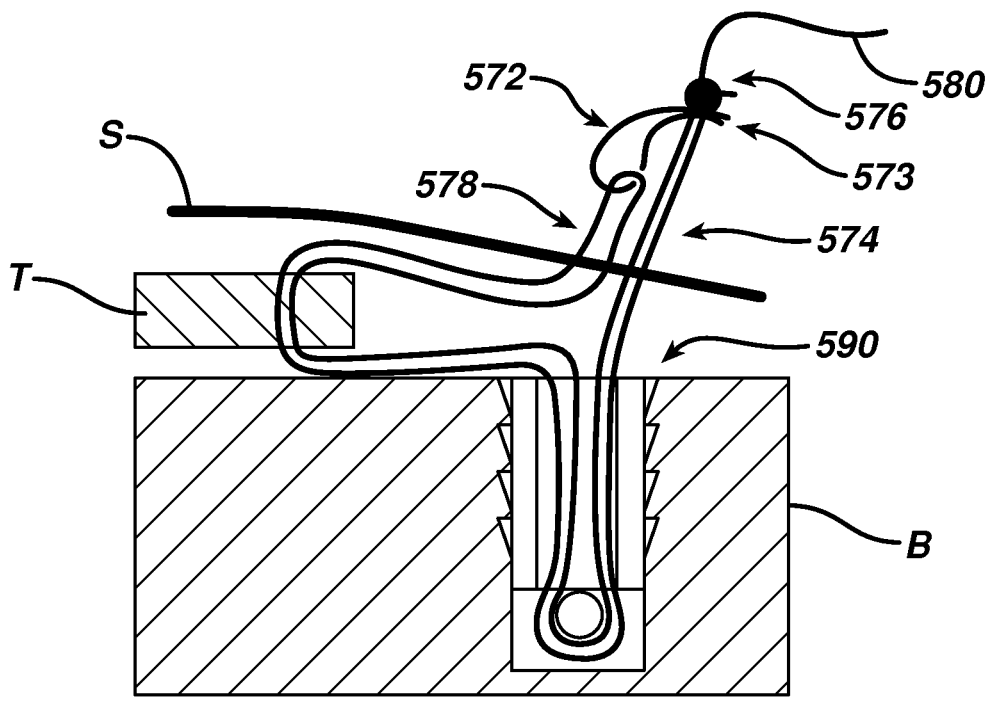
Figure 50:
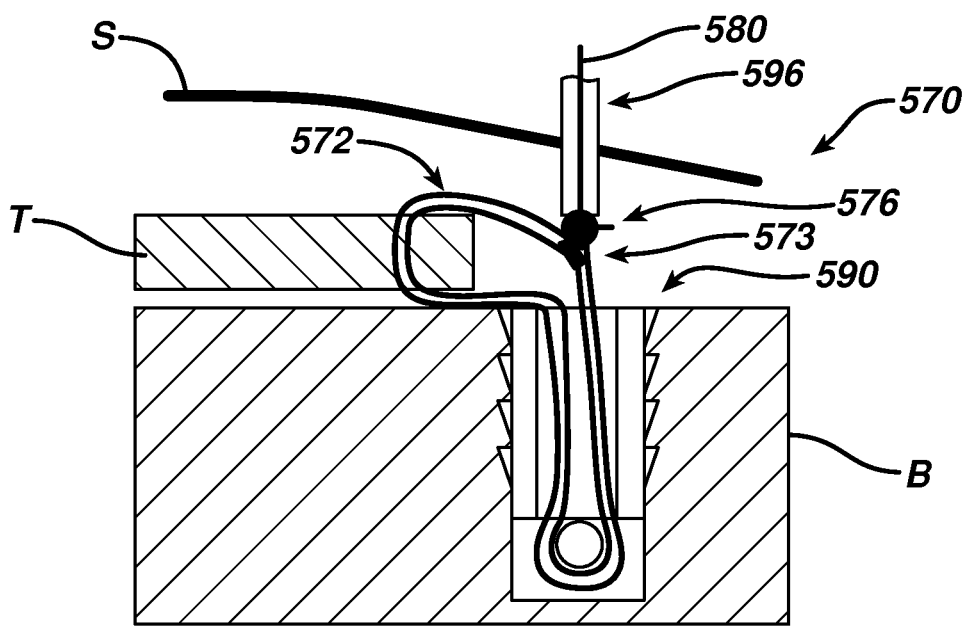

Another embodiment according to the present invention is illustrated in FIGS. 47-50. Snare assembly 570 has a fixed-length, preferably continuous loop 572 of a first filament which a surgeon or other user utilizes to form a Lark's Head knot, also known as a Bale Sling Hitch, to serve as a noose 573, FIG. 48, to grip a section of a second filament 574 as shown in FIGS. 49-50.

Figure 47:
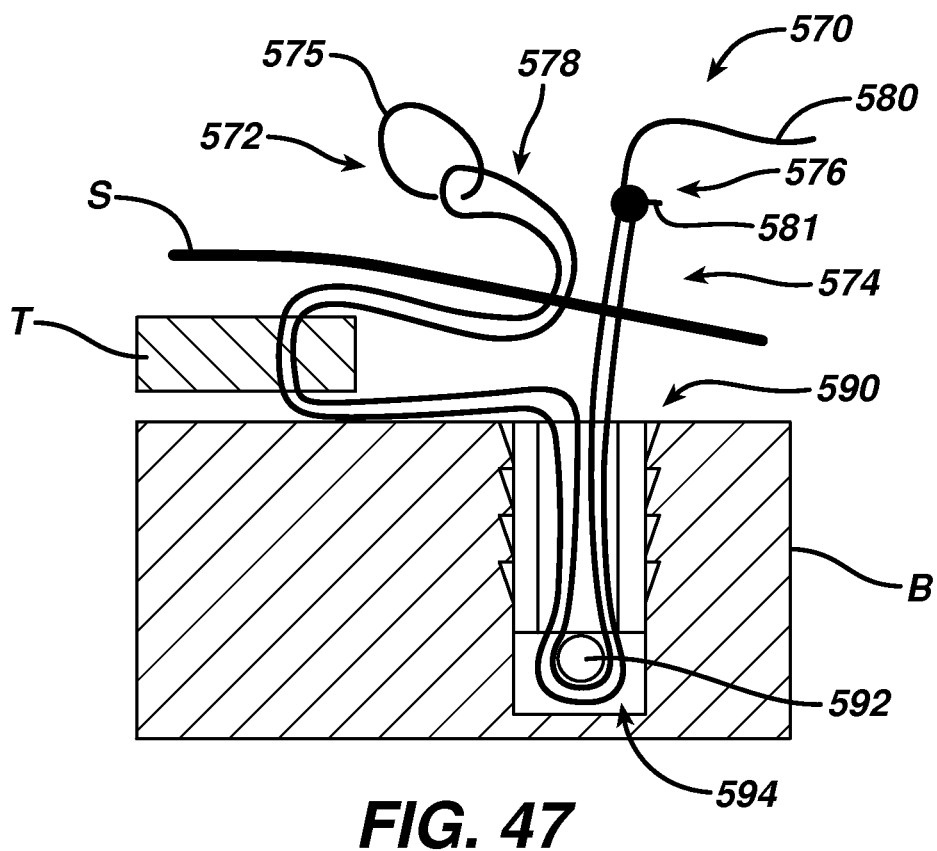
FIGS. 47-50 are schematic side views of another snare assembly according to the present invention utilizing a lark's head knot, with FIG. 48A depicting an alternative fixed-length loop.
Figure 48:
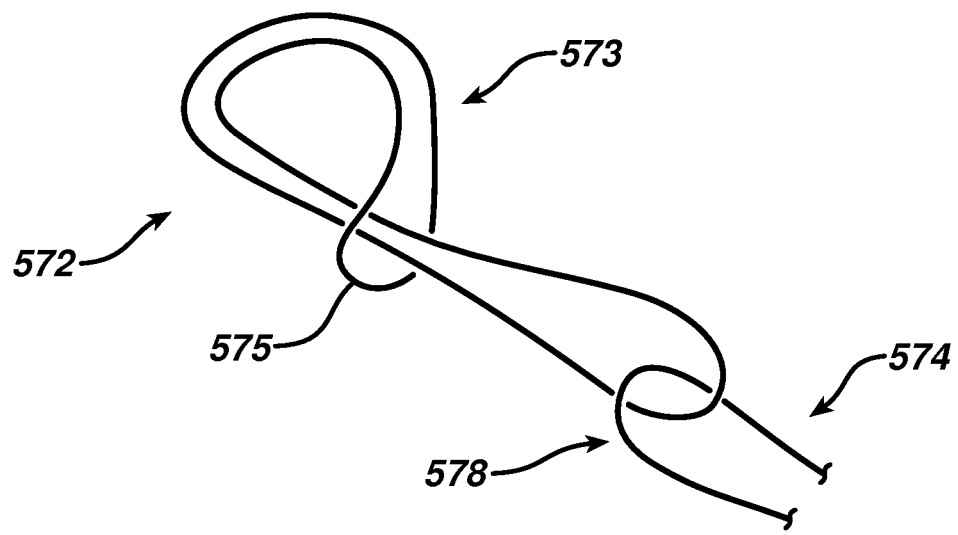

Second filament 574, FIG. 47, has a collapsible loop 578 with a sliding knot 576 such as a sliding bunt line half hitch knot, a tensioning or post limb 580, and a tag or terminal limb 581. Collapsible loop 578 passes around filament engagement feature 592, also referred to as a saddle 592, of bone anchor 590. In one construction, snare assembly 570 is manufactured in the condition shown in FIG. 47 and supplied to a user with sliding knot 576 already tied. To utilize snare assembly 570, a hole 594 is formed in bone B and the anchor 590 is inserted to the position shown in FIG. 47, and then continuous loop 572 is passed through tissue T.

After the noose 573 is formed with a Lark's Head knot, tail 580 and sliding knot 576 are passed through noose 573, FIG. 49. Noose 573 is then tightened against sliding knot 576. A knot pusher 596, FIG. 50, assists in collapsing the loop 578 to tighten the snare assembly 570 to apply tension to tissue T. Depending on the overall length of first loop 572, a portion of it may be drawn into anchor 590.

Thus, when snare assembly 570 is supplied to a surgeon or other user with sliding knot 576 already tied, snare assembly 570 serves another example according to the present invention of a pre-formed, knot-less filament system which does not require the user to manipulate free limbs to tie knots during an operation. Adding to the benefits of snare assemblies according to the present invention, including high strength and loop security, low knot profile, ability to tension incrementally, and easy use with threaded anchors, providing a loop capable of forming a Lark's Head removes altogether the burden of tying a knot near or within a patient.

Figure 48A:
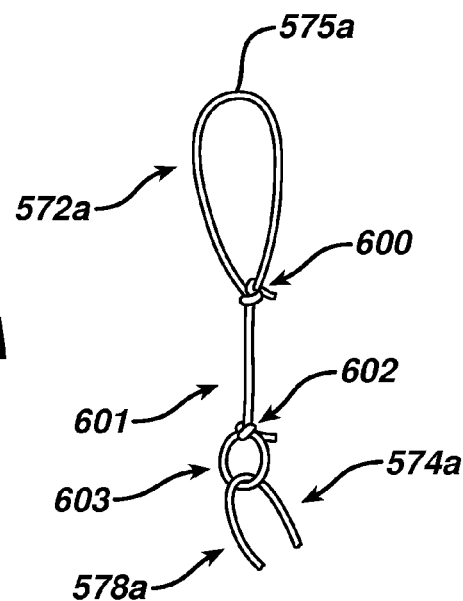
Figure 52:
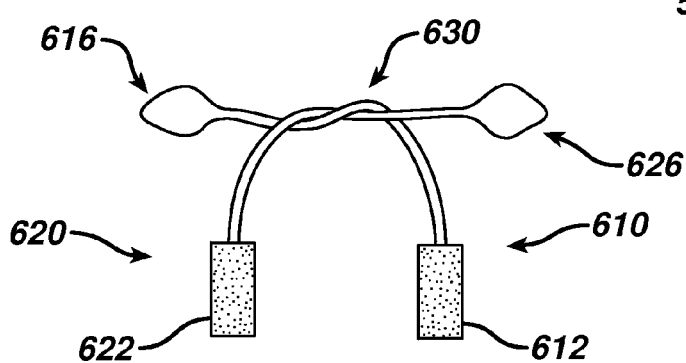
FIG. 52 shows the suture passers of FIG. 51 after the distal end of the left passer has been looped under and then over the right passer to form a simple half hitch.

In other words, a first filament, preferably a continuous fixed-length suture loop, is slidably attached to a collapsible filament loop of a second filament having a preformed sliding knot. In another construction shown in FIG. 48A, the fixed-length loop 572a is formed at one end of a first filament 601, such as by pre-tying a first bowline knot 600, and the other end of the first filament 601 is slidably attached to the second filament 574a with another, smaller loop 603, such as formed by a second, smaller pre-tied bowline knot 602 through which the collapsible loop 578a passes. After the anchor is placed in bone, the continuous-loop end with bight 575a is passed through tissue. A Lark's Head knot is then created on the continuous loop 572a, which generates a very robust noose.

One or more tools can be utilized to assist creation of the constructs described above, especially if a half hitch is desired to be thrown on free filament limbs passing through different loops of a "pretzel" noose, that is, a noose with at least one half hitch that defines multiple loops through which the free filament limbs are passed. Improved threading tools and suture passers are illustrated in FIGS. 51-57 to automatically create a simple half hitch when two filament ends are pulled through loops of a noose.

Figure 51:
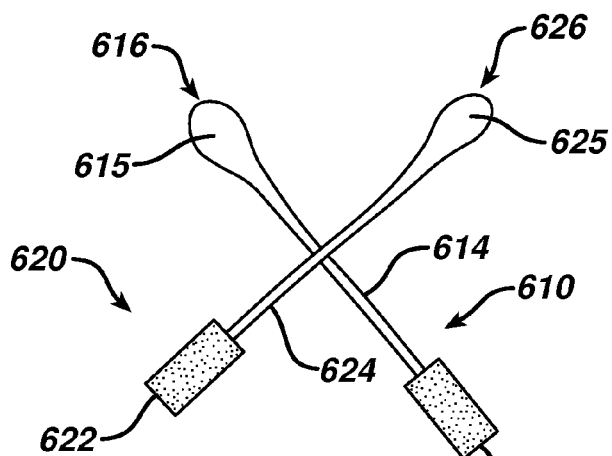
FIG. 51 is a schematic top view of two suture passers, with the left passer placed diagonally over the right passer in preparation for becoming intertwined.

Suture passer 620 is shown in FIG. 51 placed diagonally over suture passer 610. Suture passer 610 has proximal tab or handle 612, shaft 614 formed of wire or other flexible material, and opening 615 at distal end 616. Suture passer 620 has proximal handle 622, flexible shaft 624, and an opening 625 at distal end 626. Distal end 626 is looped under and around shaft 614 to create a simple half hitch 630, FIG. 52.

Figure 53A:
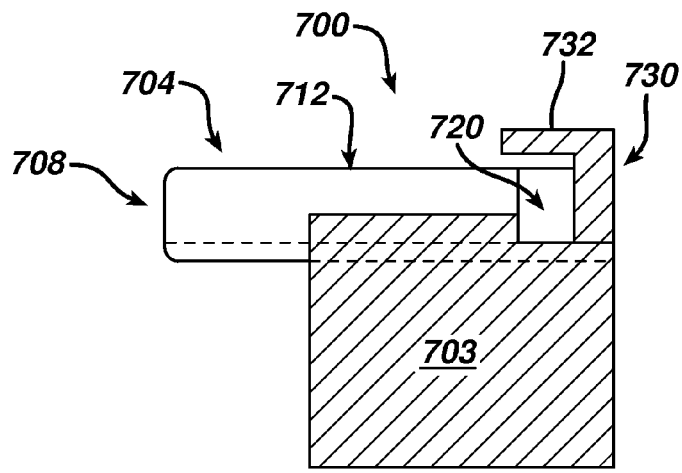
FIG. 53A is a side cross-sectional view along lines 53A-53A of FIG. 53.
Figure 53:
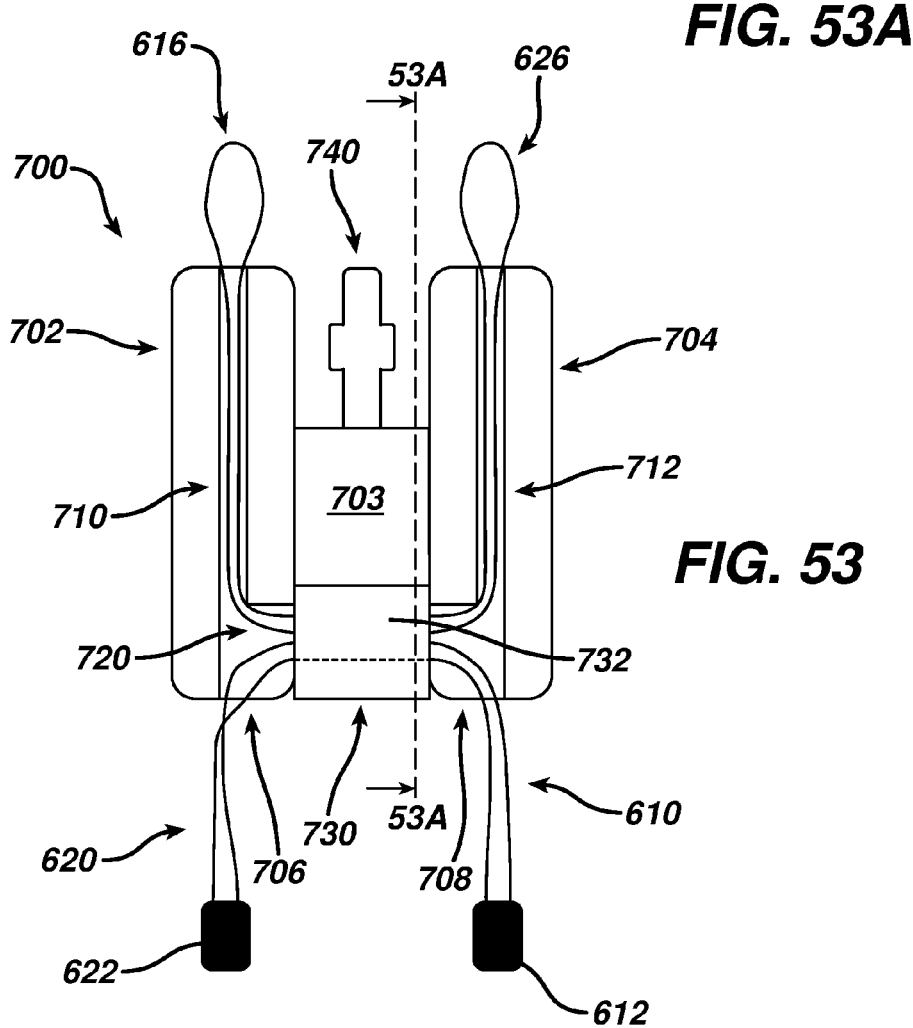
FIG. 53 is a schematic top view of an improved threader tool according to the present invention with the suture passers of FIG. 52 held within channels by a fixed stop.

Intertwined suture passers 610 and 620 are shown held by threader tool 700 in FIG. 53. Tool 700 has projections 702 and 704 which are substantially cylindrical tubes in this construction, whose distal ends are similar to tubes 102 and 104 of FIGS. 14A-14B above. Each projection 702, 704, FIGS. 53-53A, is supported by common handle 703 and has a longitudinal channel 706, 708, respectively, with slots 710, 712 to facilitate placement of filaments or passers such as suture passers 610, 620 into tool 700, and to facilitate subsequent removal of filaments drawn into tool 700 by the passers. Tool 700 further defines a common passage 720, formed in part by notches in the proximal walls of projections 702 and 704, which interconnects the proximal portions of channels 706 and 708. Half hitch 630, FIG. 52, lies within passage 720, FIG. 53, and is further held by fixed stop 730 with lip or overhang 732, which is an inverted "L" shape in this construction. Tool 700 further includes a distal finger 740 in this construction to serve as a catch or post for one or more filaments during the threading procedure, such as to hold a cinch loop or other noose in position.

In another construction shown in side view in FIG. 54, a tool 700a has a movable stop 730a with a strut 734a pivotally attached to handle 703a by pin 740 passing through the lower portion of strut 734a, or other type of hinge such as a living hinge. Tubular projection 702a is visible in this view. Stop 730a has a lip 732a supported by strut 734a. In one construction, a user manipulates stop 730a to hold or release suture passers by moving stop 730a toward or away from handle 703a as indicated by arrow 736; stop 730a is shown in phantom in an open position after being moved away from handle 703a. In another construction, a spring 742, also shown in phantom, biases stop 730a in one direction, preferably toward handle 703a. As a user pulls suture through the device, a certain amount of force causes stop 730a to overcome the biasing force of spring 742 and move away from handle 703a to assist release of the tied suture.

Several threader tools according to the present invention having intersecting channels are shown in top view in FIGS. 55-57. A V-shaped tool 800, FIG. 55, has projections 802, 804 with intersecting channels 806 and 808, respectively, and a distal finger 840. A proximal trapezoidal stop 830 holds suture passers in place as they pulled proximally. The distal portions of projections 802, 804 become substantially parallel to each other to assist removal of the tied knot from tool 800.

Tool 900, FIG. 56, has straight projection 902 and curved projection 904 that define channels 906 and 908, respectively. Stop 930 forms a proximal corner at the intersection where sutures can be pulled proximally when force is applied at right angles to respective suture passers, which is expected to ease suture movement through the channels 906, 908.

Tool 1000, FIG. 57, is a horseshoe shape to reduce forces needed to pull sutures through the tool 1000. Finger 1040 is positioned slightly below to distal opening of channels 1006, 1008 to minimize obstruction of the suture threading process.

This invention may also be expressed as a surgical filament snare assembly with a bone anchor and a first filament having a noose, formed from at least one half hitch, on a first portion of at least a first limb and having a second portion connected to the filament engagement feature of the anchor. The noose is capable of receiving at least two free filament limbs and strangulating them when tension is applied to at least one of the free filament limbs and the noose. Preferably, the assembly further includes a threader tool having at least two projections having distal ends capable of being removably inserted into different loops of the half hitch. Each projection defines a channel capable of receiving a portion of at least one free filament limb to pass it through a loop of the half hitch, and each projection further defines a slot communicating with the channel to facilitate removal of the filament limb from the tool. Each slot has the same width as its corresponding channel in some embodiments and, in other embodiments, has a different width, typically a narrower width, than that of the corresponding channel.

In certain embodiments, the projections are tubes joined together with at least one handle for manipulation the tube. The proximal ends of the channels are connected by one of an intersection and a common passage, and the tool further includes a stop as a proximal portion of the one of the intersection and the common passage. In some embodiments, the stop is movable, and may include a spring to bias the stop toward the intersection or common passage.

In yet other embodiments, the assembly further includes at least two suture passers having distal ends for engaging portions of the free filament limbs, and the suture passers being capable of pulling the free filament limbs through the channels when proximal-directed force is applied to proximal ends of the suture passers. Preferably, the distal ends of the suture passers are intertwined in at least one half hitch to impart at least one half hitch to the free filament limbs when they are drawn through the tool. Different combinations selected from the group of an anchor, one or more filament constructs as described herein, a threader tool, and one or more suture passers can also be referred to as different kits according to the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A surgical filament snare assembly, comprising:
   an anchor capable of being fixated in bone and having a filament engagement feature;
   a first filament that is a braided suture, the first filament having a noose with first and second noose limbs connected to the filament engagement feature of the anchor and emerging from the anchor as first and second free filament limbs which are capable of being passed through tissue to be repaired and then passable through the noose to enable incremental tensioning of the tissue after the anchor is fixated in bone, the noose strangulating the free filament limbs when tension is applied to at least one of the free filament limbs and the noose; and
   a flexible sleeve joining at least some portion of the first and second free filament limbs to facilitate passing of the free filament limbs through tissue and then the noose as a single unit,
   wherein a section of one of the first and second free limbs serves as the sleeve and the sleeve section has fewer picks per unit length than the picks per unit length for the remainder of the first filament.

2. The assembly of claim 1 wherein the sleeve is formed from a braided suture.

3. The assembly of claim 1 wherein the noose is retractable toward the anchor.

4. The assembly of claim 1 wherein the noose is formed from at least one half hitch.

5. The assembly of claim 1 further including at least one tube capable of being removably inserted into the noose to provide a passage for the end of at least one of the free filament limbs.

6. A surgical filament snare assembly, comprising:
   an anchor capable of being fixated in bone and having a filament engagement feature;
   a first filament having a noose with first and second noose limbs extending from the noose, the first and second noose limbs being in contact with the filament engagement feature of the anchor and emerging from the anchor as first and second free filament limbs that are capable of being passed through tissue to be repaired and then passable through the noose to enable incremental tensioning of the tissue after the anchor is fixated in bone, the noose strangulating the free filament limbs when tension is applied to at least one of the free filament limbs and the noose; and
   a flexible sleeve joining at least some portion of the first and second free filament limbs to facilitate passing of the free filament limbs through tissue and then the noose as a single unit,
   wherein a closure point of the noose is separate from an entry point of the first filament into the sleeve, the entry point of the first filament into the sleeve being at a location along the sleeve that is more proximate to the noose than is an exit point of the first filament from the sleeve.

7. The assembly of claim 6 wherein the sleeve is formed from a braided suture.

8. The assembly of claim 6 wherein the first filament is a braided suture and a section of one of the first and second free filament limbs serves as the sleeve.

9. The assembly of claim 8 wherein the sleeve section has fewer picks per unit length than the picks per unit length for the remainder of the first filament.

10. The assembly of claim 6 wherein the sleeve is positioned over the entire portion of the first and second free filament limbs before implantation of the anchor in a patient.

11. The assembly of claim 10 wherein the sleeve is further positioned beyond the filament engagement feature to cover at least some of the first and second noose limbs.

12. The assembly of claim 6 wherein the noose is retractable toward the anchor.

13. The assembly of claim 6 wherein the noose is formed from at least one half hitch.

14. The assembly of claim 6 further including at least one tube capable of being removably inserted into the noose to provide a passage for the end of at least one of the free filament limbs.

* * * * *